United States Patent
Ng

(10) Patent No.: US 8,708,988 B2
(45) Date of Patent: Apr. 29, 2014

(54) ABSORBENT ARTICLE CONFIGURED FOR CONTROLLED DEFORMATION

(75) Inventor: Meijia Ng, Singapore (SG)

(73) Assignee: Kimberly-Clark Worldwide, Inc., Neenah, WI (US)

( * ) Notice: Subject to any disclaimer, the term of this patent is extended or adjusted under 35 U.S.C. 154(b) by 482 days.

(21) Appl. No.: 12/959,606

(22) Filed: Dec. 3, 2010

(65) Prior Publication Data

US 2012/0143163 A1 Jun. 7, 2012

(51) Int. Cl.
*A61F 13/15* (2006.01)

(52) U.S. Cl.
USPC ............... 604/385.101; 604/385.01

(58) Field of Classification Search
USPC ............. 604/361, 385.01, 385.101, 385.11, 604/385.14, 385.16
See application file for complete search history.

(56) References Cited

U.S. PATENT DOCUMENTS

| | | | |
|---|---|---|---|
| 2,681,032 A | 6/1954 | Shaw | |
| 3,338,992 A | 8/1967 | Kinney | |
| 3,341,394 A | 9/1967 | Kinney | |
| 3,371,668 A | 3/1968 | Johnson | |
| 3,502,538 A | 3/1970 | Petersen | |
| 3,502,763 A | 3/1970 | Hartmann | |
| 3,542,615 A | 11/1970 | Dobo et al. | |
| 3,556,932 A | 1/1971 | Coscia et al. | |
| 3,556,933 A | 1/1971 | Williams et al. | |
| 3,692,618 A | 9/1972 | Dorschner et al. | |
| 3,802,817 A | 4/1974 | Matsuki et al. | |
| 3,849,241 A | 11/1974 | Butin et al. | |
| 4,246,900 A | 1/1981 | Schroder | |
| 4,340,563 A | 7/1982 | Appel et al. | |
| 4,357,938 A | 11/1982 | Ito et al. | |
| 4,418,524 A | 12/1983 | Ito et al. | |
| 4,447,240 A | 5/1984 | Ito et al. | |
| 4,488,928 A | 12/1984 | Ali Khan et al. | |
| 4,623,342 A | 11/1986 | Ito et al. | |
| 4,640,859 A | 2/1987 | Hansen et al. | |
| 4,675,394 A | 6/1987 | Solarek et al. | |
| 4,701,173 A | 10/1987 | Zehner et al. | |
| 4,738,677 A | 4/1988 | Foreman | |
| 4,753,646 A | 6/1988 | Enloe | |
| 4,779,456 A | 10/1988 | Cantoni | |
| 4,781,731 A | 11/1988 | Schlinger | |
| 4,787,896 A | 11/1988 | Houghton et al. | |
| 4,809,493 A | 3/1989 | Genba et al. | |
| 4,834,733 A | 5/1989 | Huntoon et al. | |
| 4,911,701 A | 3/1990 | Mavinkurve | |
| 4,981,557 A | 1/1991 | Bjorkquist | |
| 5,007,906 A | 4/1991 | Osborn, III et al. | |
| 5,008,344 A | 4/1991 | Bjorkquist | |
| 5,026,364 A | 6/1991 | Robertson | |
| 5,085,736 A | 2/1992 | Bjorkquist | |
| 5,122,407 A | 6/1992 | Yeo et al. | |
| 5,160,331 A | 11/1992 | Forester et al. | |

(Continued)

FOREIGN PATENT DOCUMENTS

| | | |
|---|---|---|
| CN | CND 3251084 | 8/2002 |
| EP | 0 220 741 A2 | 5/1987 |

(Continued)

*Primary Examiner* — Lynne Anderson
(74) *Attorney, Agent, or Firm* — Kimberly-Clark Worldwide, Inc.

(57) ABSTRACT

The present disclosure provides an absorbent article including an absorbent core and at least one barrier structure having a fluid shrinkable string attached thereto, wherein insult of the fluid shrinkable string by the user causes deformation of the peripheral edge of the barrier structure in the z-direction forming a leakage barrier between the user and the peripheral edge of the barrier structure.

20 Claims, 12 Drawing Sheets

(56) References Cited

U.S. PATENT DOCUMENTS

| | | |
|---|---|---|
| 5,176,672 A | 1/1993 | Bruemmer et al. |
| 5,181,563 A | 1/1993 | Amaral |
| 5,260,345 A | 11/1993 | Desmarais et al. |
| 5,330,598 A | 7/1994 | Erdman et al. |
| 5,334,176 A | 8/1994 | Buenger et al. |
| 5,397,316 A | 3/1995 | LaVon et al. |
| 5,415,640 A | 5/1995 | Kirby et al. |
| 5,447,507 A | 9/1995 | Yamamoto |
| 5,514,121 A | 5/1996 | Roe et al. |
| 5,520,674 A | 5/1996 | Lavon et al. |
| 5,527,303 A | 6/1996 | Milby, Jr. et al. |
| 5,575,785 A | 11/1996 | Gryskiewicz et al. |
| 5,591,150 A | 1/1997 | Olsen et al. |
| 5,593,401 A | 1/1997 | Sosalla et al. |
| 5,779,860 A | 7/1998 | Hollenberg et al. |
| 5,833,680 A | 11/1998 | Hartman |
| 5,858,515 A | 1/1999 | Stokes et al. |
| 5,885,264 A | 3/1999 | Matsushita |
| 5,997,520 A | 12/1999 | Ahr et al. |
| 6,045,900 A | 4/2000 | Haffner et al. |
| 6,071,580 A | 6/2000 | Bland et al. |
| 6,114,597 A | 9/2000 | Romare |
| 6,133,501 A | 10/2000 | Hallock et al. |
| 6,168,583 B1 | 1/2001 | Tanji et al. |
| 6,175,056 B1 | 1/2001 | Carlucci et al. |
| 6,217,563 B1 | 4/2001 | Van Gompel et al. |
| D448,476 S | 9/2001 | Page et al. |
| 6,293,935 B1 | 9/2001 | Kimura et al. |
| D448,846 S | 10/2001 | Page et al. |
| 6,296,628 B1 | 10/2001 | Mizutani |
| 6,306,818 B1 | 10/2001 | Anderson et al. |
| 6,315,765 B1 | 11/2001 | Datta et al. |
| 6,326,525 B1 | 12/2001 | Hamajima et al. |
| 6,346,097 B1 | 2/2002 | Blaney |
| 6,348,047 B1 | 2/2002 | Harper |
| 6,387,084 B1 | 5/2002 | VanGompel et al. |
| 6,392,117 B1 | 5/2002 | Mayer et al. |
| 6,429,261 B1 | 8/2002 | Lang et al. |
| 6,432,097 B1 | 8/2002 | Ahr et al. |
| 6,436,081 B1 | 8/2002 | Wada et al. |
| 6,444,214 B1 | 9/2002 | Cole et al. |
| 6,521,811 B1 | 2/2003 | Lassen et al. |
| 6,537,663 B1 | 3/2003 | Chang et al. |
| 6,548,592 B1 | 4/2003 | Lang et al. |
| 6,551,297 B2 | 4/2003 | Tanaka et al. |
| 6,579,570 B1 | 6/2003 | Lang et al. |
| 6,585,712 B2 | 7/2003 | Yoshimasa |
| 6,599,848 B1 | 7/2003 | Chen et al. |
| 6,620,144 B1 | 9/2003 | Glasgow et al. |
| 6,627,670 B2 | 9/2003 | Mork et al. |
| 6,632,205 B1 | 10/2003 | Sauer |
| 6,653,406 B1 | 11/2003 | Soerens et al. |
| 6,664,436 B2 | 12/2003 | Topolkaraev et al. |
| 6,666,850 B1 | 12/2003 | Ahr et al. |
| 6,683,143 B1 | 1/2004 | Mumick et al. |
| 6,713,414 B1 | 3/2004 | Pomplun et al. |
| 6,727,004 B2 | 4/2004 | Goulet et al. |
| 6,761,709 B2 | 7/2004 | Morman et al. |
| 6,786,893 B2 | 9/2004 | Strand |
| 6,786,895 B1 | 9/2004 | Schmitz |
| 6,815,502 B1 | 11/2004 | Lang et al. |
| 6,840,925 B2 | 1/2005 | Mishima et al. |
| 6,908,458 B1 | 6/2005 | Sauer et al. |
| 6,955,667 B2 | 10/2005 | Tanaka et al. |
| 6,958,430 B1 | 10/2005 | Marinelli |
| D521,149 S | 5/2006 | Adams et al. |
| 7,037,298 B2 | 5/2006 | Ohshima et al. |
| 7,083,604 B2 | 8/2006 | Sakaguchi |
| 7,145,054 B2 | 12/2006 | Zander et al. |
| 7,176,344 B2 | 2/2007 | Gustafson et al. |
| 7,179,247 B2 | 2/2007 | Mizutani et al. |
| 7,252,870 B2 | 8/2007 | Anderson et al. |
| 7,314,967 B2 | 1/2008 | Ashton et al. |
| D567,369 S | 4/2008 | Gilroy |
| 7,358,282 B2 | 4/2008 | Krueger et al. |
| 7,491,864 B2 | 2/2009 | Nishizawa et al. |
| D600,802 S | 9/2009 | Hood et al. |
| D600,803 S | 9/2009 | Hood et al. |
| D600,805 S | 9/2009 | Hood et al. |
| 7,621,899 B2 | 11/2009 | Fujikawa et al. |
| 7,847,145 B2 | 12/2010 | Kurita et al. |
| 2001/0029359 A1 | 10/2001 | Carlucci |
| 2002/0128625 A1 | 9/2002 | Tanaka et al. |
| 2003/0050614 A1 | 3/2003 | D'Acchioli et al. |
| 2003/0163104 A1 | 8/2003 | Tears et al. |
| 2005/0010185 A1 | 1/2005 | Mizutani et al. |
| 2005/0124956 A1 | 6/2005 | Suzuki |
| 2006/0116651 A1 | 6/2006 | Kurita et al. |
| 2006/0148917 A1 | 7/2006 | Radwanski et al. |
| 2006/0246272 A1 | 11/2006 | Zhang et al. |
| 2006/0282059 A1 | 12/2006 | Fujikawa et al. |
| 2006/0287635 A1 | 12/2006 | Angel |
| 2007/0043027 A1 | 2/2007 | Rueckle et al. |
| 2007/0093772 A1 | 4/2007 | Koyama et al. |
| 2007/0225671 A1 | 9/2007 | Angel |
| 2007/0287973 A1 | 12/2007 | Cohen et al. |
| 2008/0065035 A1 | 3/2008 | Perneborn |
| 2008/0269703 A1 | 10/2008 | Collins et al. |
| 2009/0036854 A1 | 2/2009 | Guidotti et al. |
| 2009/0054760 A1 | 2/2009 | Burke |
| 2009/0054860 A1 | 2/2009 | Young et al. |
| 2009/0157022 A1 | 6/2009 | MacDonald et al. |
| 2009/0157032 A1 | 6/2009 | MacDonald et al. |
| 2009/0204095 A1 | 8/2009 | McDaniel |
| 2009/0240220 A1 | 9/2009 | MacDonald et al. |
| 2009/0299312 A1 | 12/2009 | MacDonald et al. |
| 2009/0326495 A1 | 12/2009 | MacDonald et al. |
| 2010/0147203 A1 | 6/2010 | MacDonald et al. |
| 2010/0152642 A1 | 6/2010 | Kim et al. |
| 2010/0152690 A1 | 6/2010 | Ong et al. |
| 2010/0152692 A1 | 6/2010 | Ong et al. |

FOREIGN PATENT DOCUMENTS

| | | |
|---|---|---|
| EP | 0 554 565 A1 | 8/1993 |
| EP | 0 557 047 A1 | 8/1993 |
| EP | 0 815 816 A1 | 1/1998 |
| EP | 0 815 821 A2 | 1/1998 |
| EP | 0 846 454 A1 | 6/1998 |
| EP | 1 206 923 A1 | 5/2002 |
| EP | 0 869 758 B1 | 8/2002 |
| EP | EM 000772975-0028 | 11/2008 |
| GB | 2 244 653 A | 12/1991 |
| GB | D 2 078 590 | 2/1999 |
| JP | 02-107249 A | 4/1990 |
| JP | 03-185197 A | 8/1991 |
| JP | 2001-017467 A | 1/2001 |
| JP | 2004-041339 A | 2/2004 |
| JP | 1233575 S | 3/2005 |
| JP | 2006-334113 A | 12/2006 |
| JP | 1318295 S | 12/2007 |
| WO | WO 94/02095 A1 | 2/1994 |
| WO | WO 95/25493 A1 | 9/1995 |
| WO | WO 97/14389 A1 | 4/1997 |
| WO | WO 97/40798 A1 | 11/1997 |
| WO | WO 97/40803 A1 | 11/1997 |
| WO | WO 97/46185 A1 | 12/1997 |
| WO | WO 00/00145 A2 | 1/2000 |
| WO | WO 00/53830 A1 | 9/2000 |
| WO | WO 2005/016103 A1 | 2/2005 |
| WO | WO 2006/021763 A1 | 3/2006 |
| WO | WO 2007/073254 A1 | 6/2007 |
| WO | WO 2007/125352 A1 | 11/2007 |

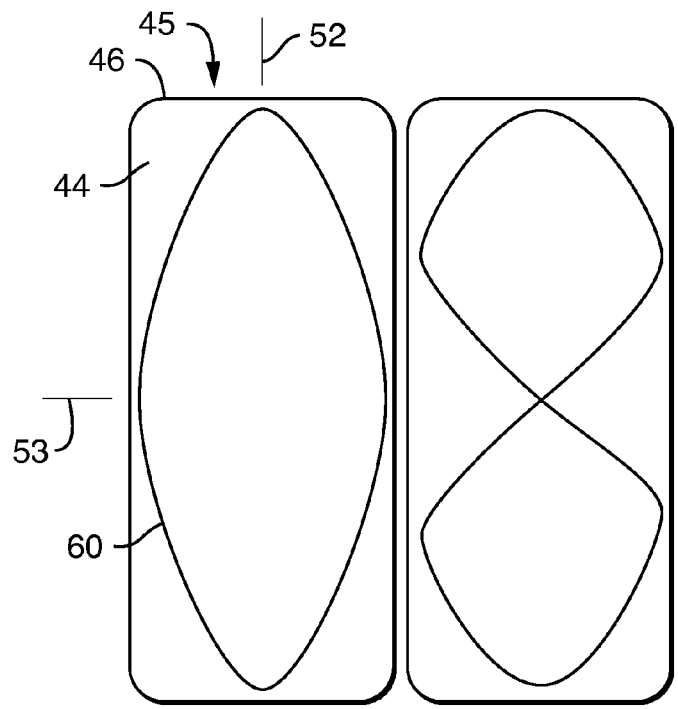
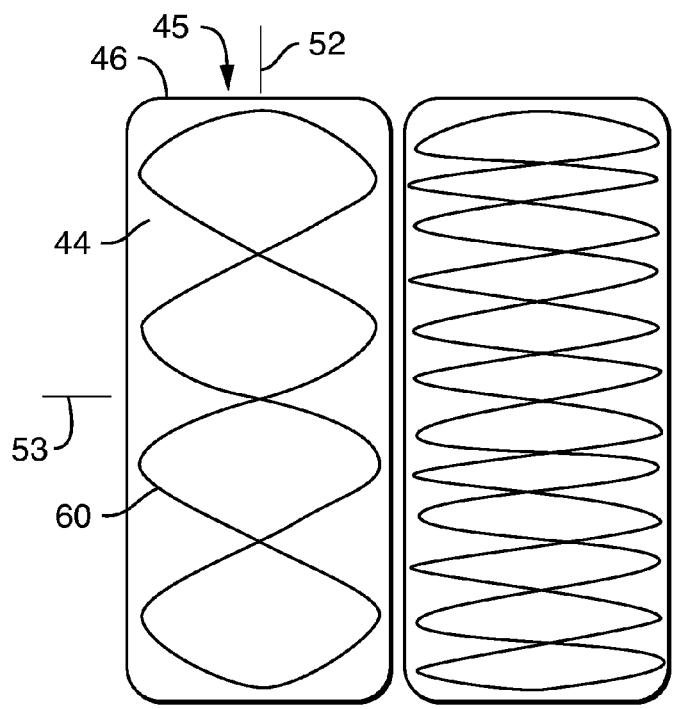
FIG. 5A    FIG. 5B
FIG. 5C    FIG. 5D

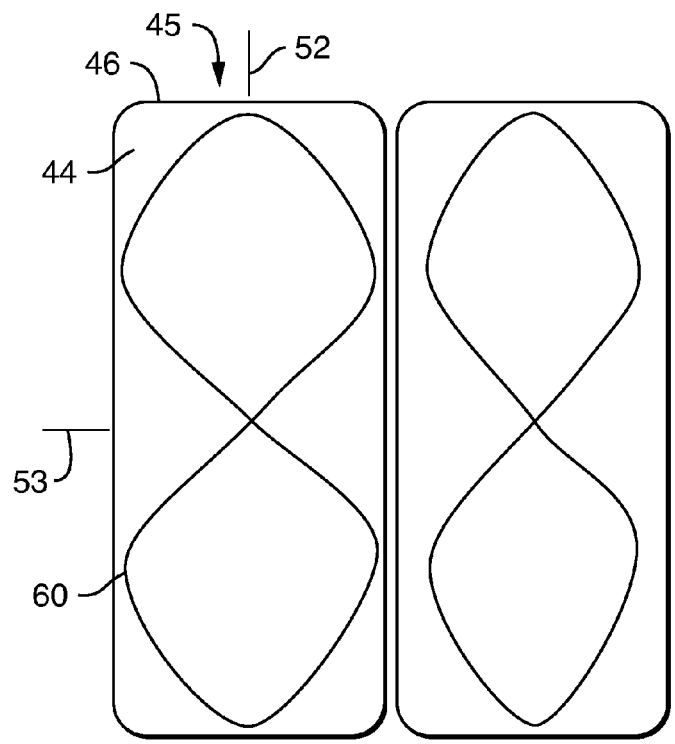
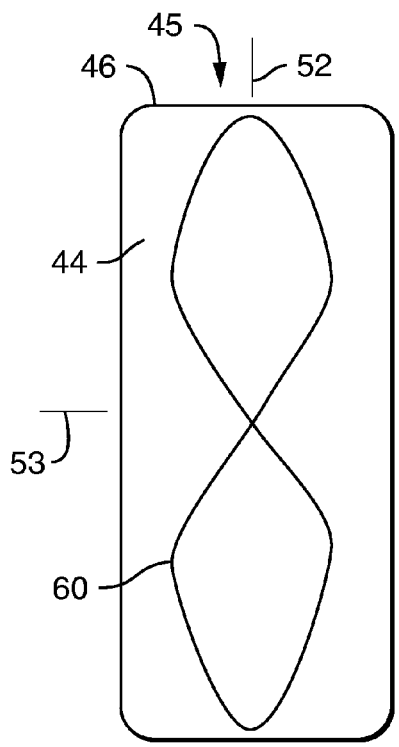

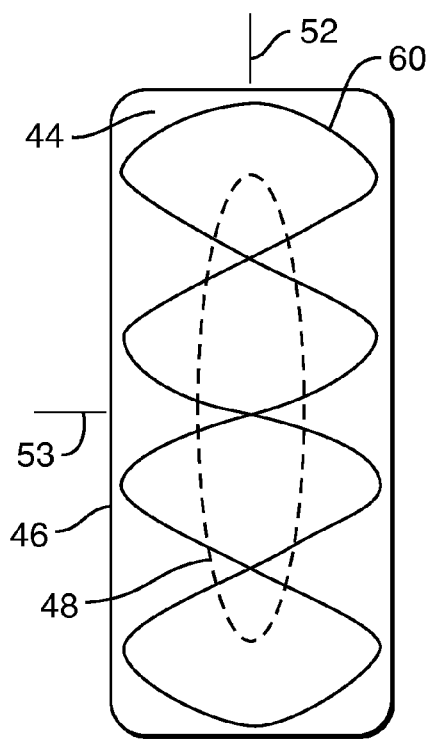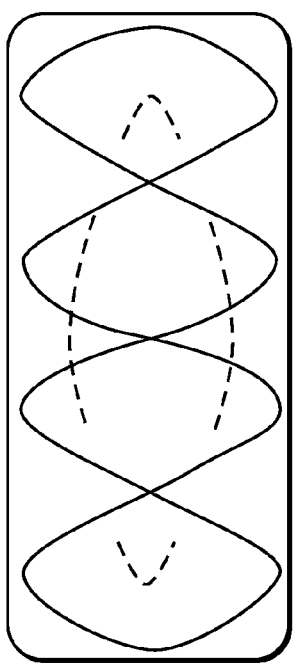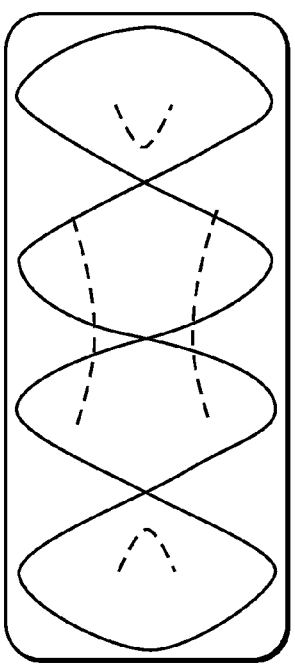
FIG. 11A  FIG. 11B  FIG. 11C
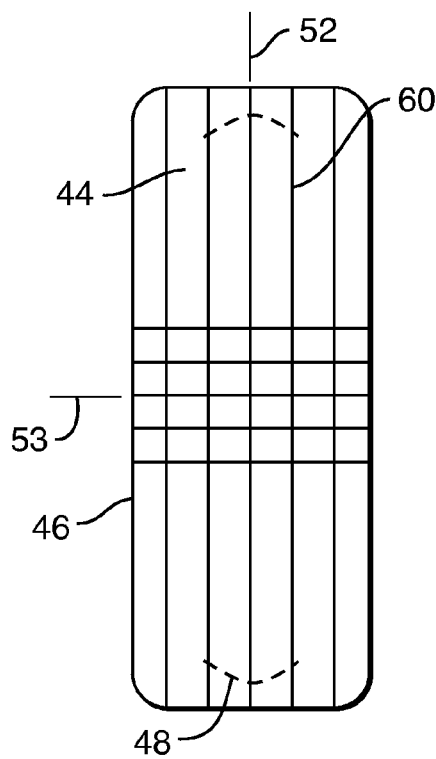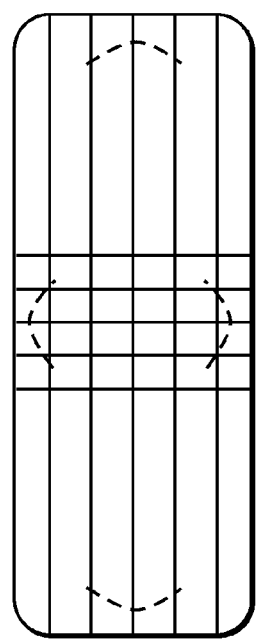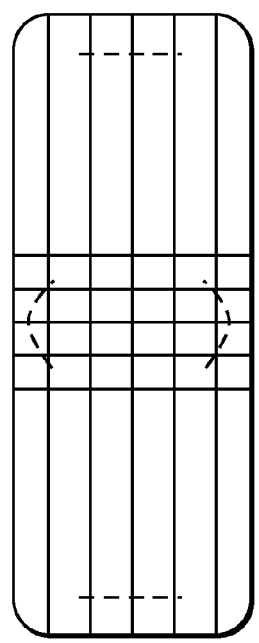
FIG. 12A  FIG. 12B  FIG. 12C

ABSORBENT ARTICLE CONFIGURED FOR CONTROLLED DEFORMATION

TECHNICAL FIELD

The present disclosure relates generally to an absorbent article and more specifically to a feminine care pad having a deformable barrier structure, the barrier structure being deformed by the shrinking of a fluid shrinkable string attached thereto when insulted by the user.

BACKGROUND

Absorbent articles such as feminine care products, incontinence products, and training pants are useful to absorb and contain body wastes. These products have developed to the extent that body exudates are quickly drawn and retained away from the wearer's skin so that the wearer remains relatively dry and comfortable. Although this improved performance enhances wearer dryness and comfort, the article can still be subject to leakage, particularly during a fluid insult gush, or when the article is becoming full. In one example, adult care wearers, especially women, are very concerned about leakage in public. Some wearers may be so bothered by leakage that if it occurs in a public place, they will avoid that place and situation for the rest of their life. Leakage is therefore a very undesirable characteristic in an adult care product.

Similarly, leakage from catamenial products poses a major problem to women and can be a social embarrassment, especially if it happens in public places. Current products exist that can delay or minimize leakage through length extension, material use, etc. There exist, however, situations in which women unexpectedly experience a gush of fluid, or unknowingly wear catamenial products beyond leakage points and risk staining their clothes. A woman might also make several trips to the bathroom to check her pad for fear of leakage. Such behavior can make menstruation a more inconvenient experience than it needs to be.

In an attempt to reduce or eliminate the occurrence of leakage, it may be desirable to maintain absorbent articles in close contact with the wearer's body. Such close body fit can allow the absorbent article to absorb body exudates at their source. Achieving close body fit limits the chance for the body exudates to flow off of or out of the absorbent article. However, good body contact may not always be available, particularly along the side regions of an article, which can lead to leakage. In attempts to address this issue, leakage protection features have been included in articles, however, these barriers tend to add bulk to the product, while others are easily flattened during use, making the article uncomfortable, less effective, or both. Users may also be overly conscious and agitated when wearing such articles. Thus, there is a need for an absorbent article which provides close body fit and/or better leak protection, particularly after a fluid insult, without creating undesirable bulk.

SUMMARY

In response to the needs discussed above, a new absorbent article has been developed, which will allow women to maintain their active lifestyle with confidence, even on heavy-flow days. In general, the invention provides an absorbent article comprising a barrier that is deformed in three dimensions when insulted, resulting in good body fit and leakage protection.

The barrier structures presented in the invention have the ability to stay flat before usage, hence increasing the level of comfort to the user. However, upon insult of the fluid shrinkable string by the user the peripheral edge of the barrier structure is deformed in the z-direction forming a leakage barrier between the user and the peripheral edge of the barrier structure. Thus, the structure and arrangement of the fluid shrinkable string enables the barrier structure to be deformed, taking on a three dimensional shape, resulting in a closer body fit and increasing the tendency of fluid to be maintained within the pad and reducing the possibility of leakage.

In some aspects the absorbent article comprises an absorbent core having a garment facing surface and a body facing surface; a deformable barrier structure positioned adjacent to the body facing surface of the absorbent core, the barrier structure having a longitudinal direction, a transverse direction, a longitudinally-extending centerline, a transverse-extending centerline, and a peripheral edge; and a fluid shrinkable string attached to the deformable barrier structure in a pattern capable of providing forces to the barrier structure in both the longitudinal and transverse direction when insulted by a user.

In other aspects the absorbent article comprises an absorbent core having a garment facing surface and a body facing surface; a deformable barrier structure adjacent to the body facing surface of the absorbent core, the barrier structure having a peripheral edge; and a fluid shrinkable string attached to the deformable barrier structure in a pattern capable of deforming the peripheral edge of the barrier structure in the z-direction from about 1 to about 40 mm when measured from the body facing surface of the absorbent core thereby forming a leakage barrier between the peripheral edge and the user.

In still other aspects the absorbent article has a longitudinal direction, a transverse direction, a longitudinally-extending centerline, and a transverse-extending centerline, the absorbent article comprising at least two absorbent cores in spaced apart relation to one another; and at least one fluid shrinkable string spanning the at least two spaced apart absorbent cores, wherein insult of the fluid shrinkable string by the user causes repositioning of the at least two spaced apart absorbent cores.

Numerous other features and advantages of the present invention will appear from the following description.

FIGURES

The foregoing and other features, aspects and advantages of the present invention will become better understood with regard to the following description, appended claims and accompanying drawings where:

Figures 7A, 7B:
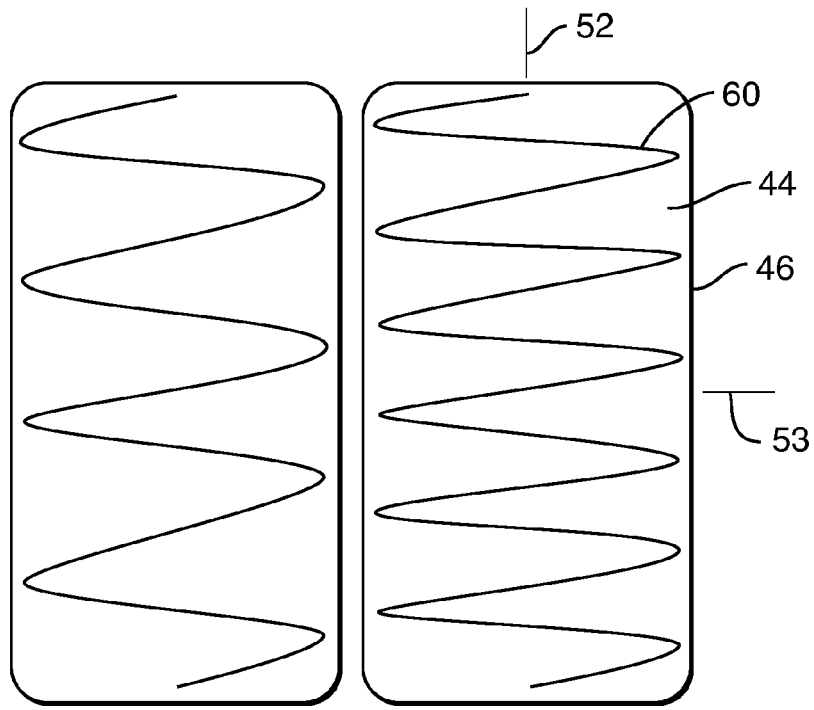
Figure 8:
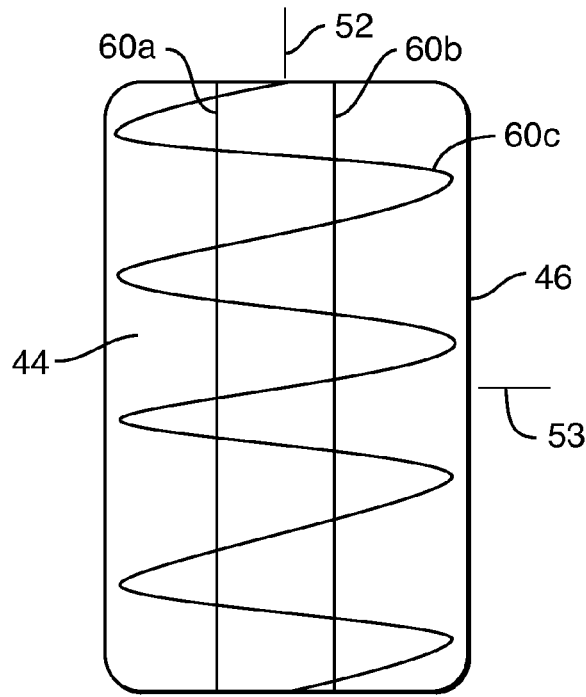
Figures 9A, 9B:
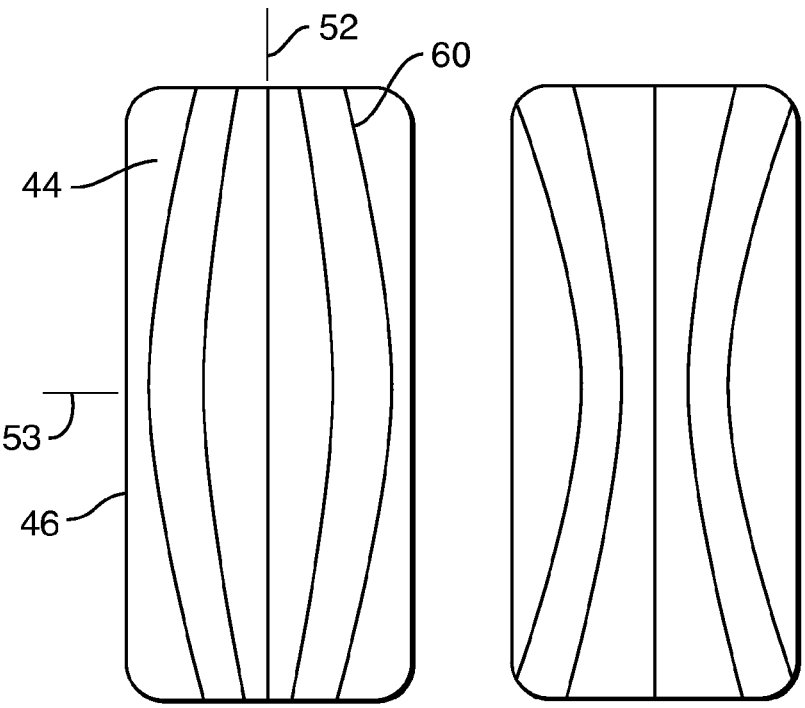
Figures 10A, 10B, 10C:
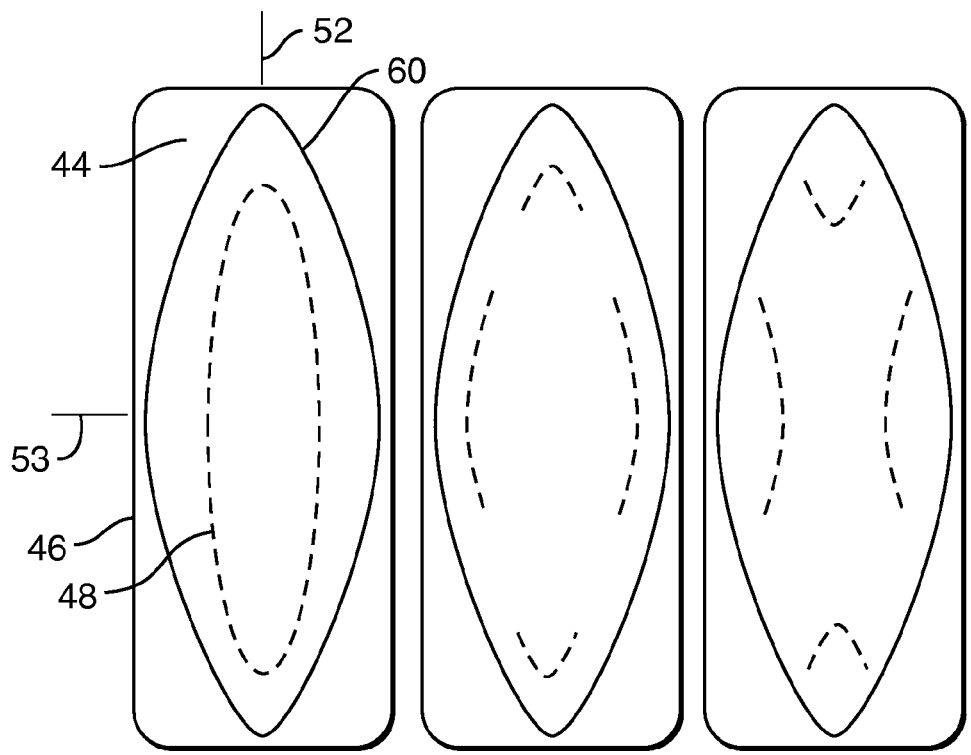
Figures 13, 14A:
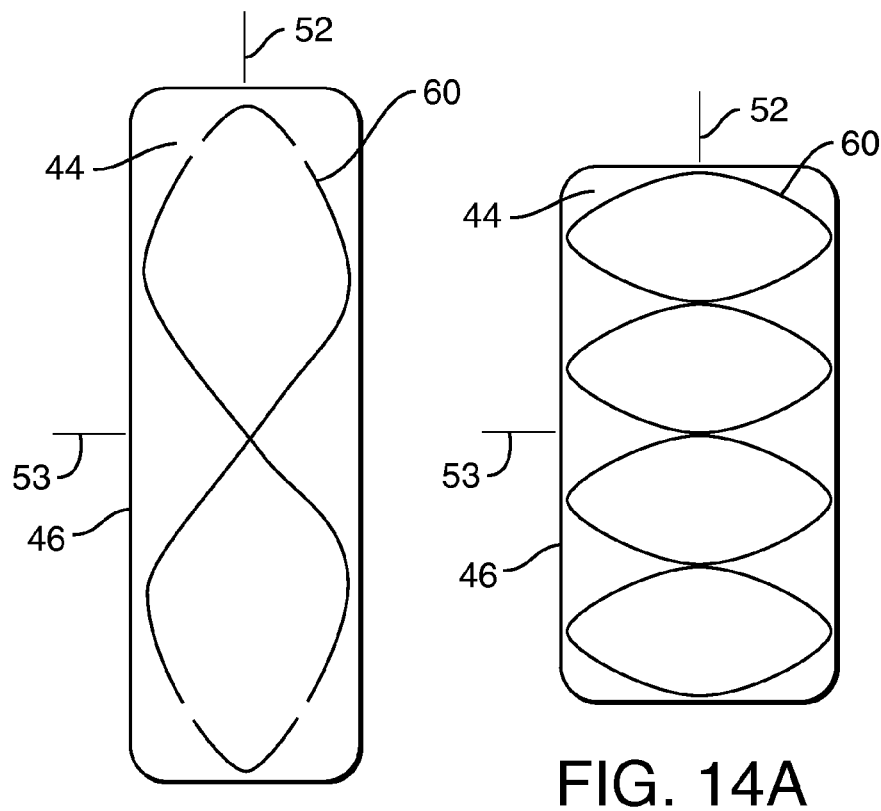
Figures 14B, 14C, 14D:
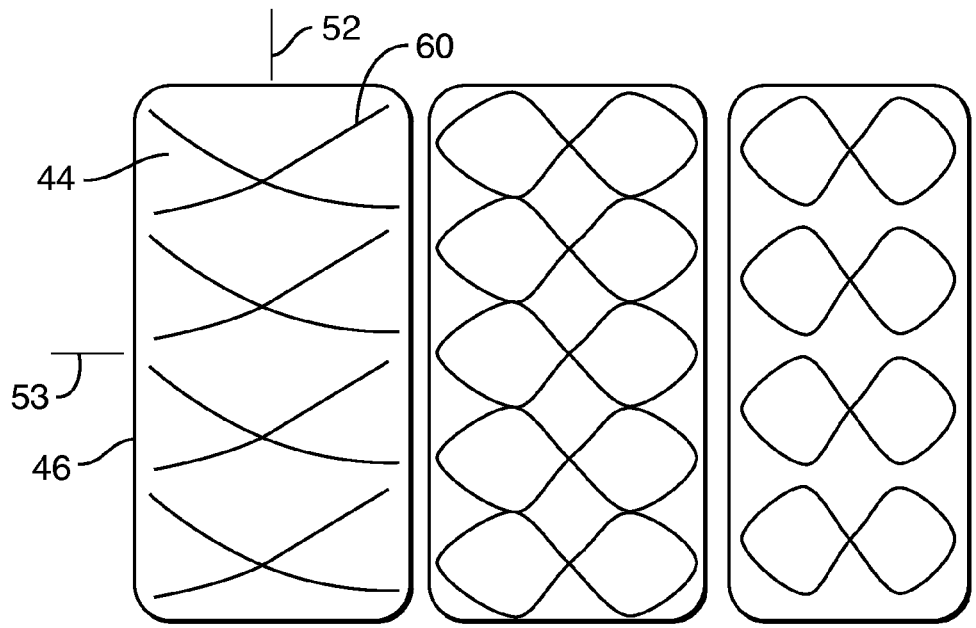
Figures 15A, 15B, 15C:
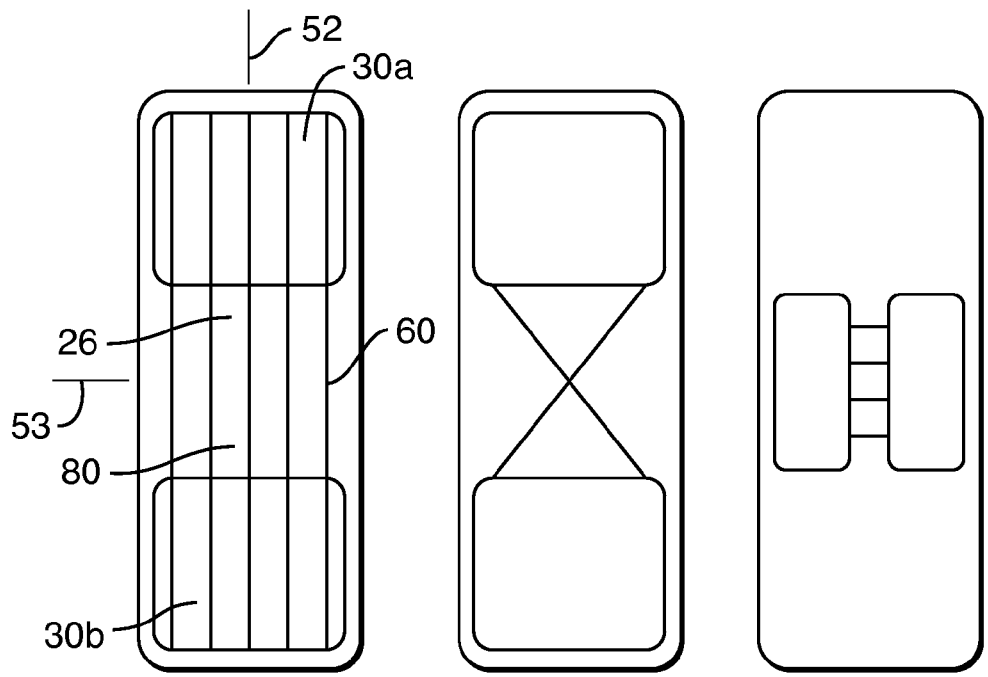
Figures 16A, 16B:
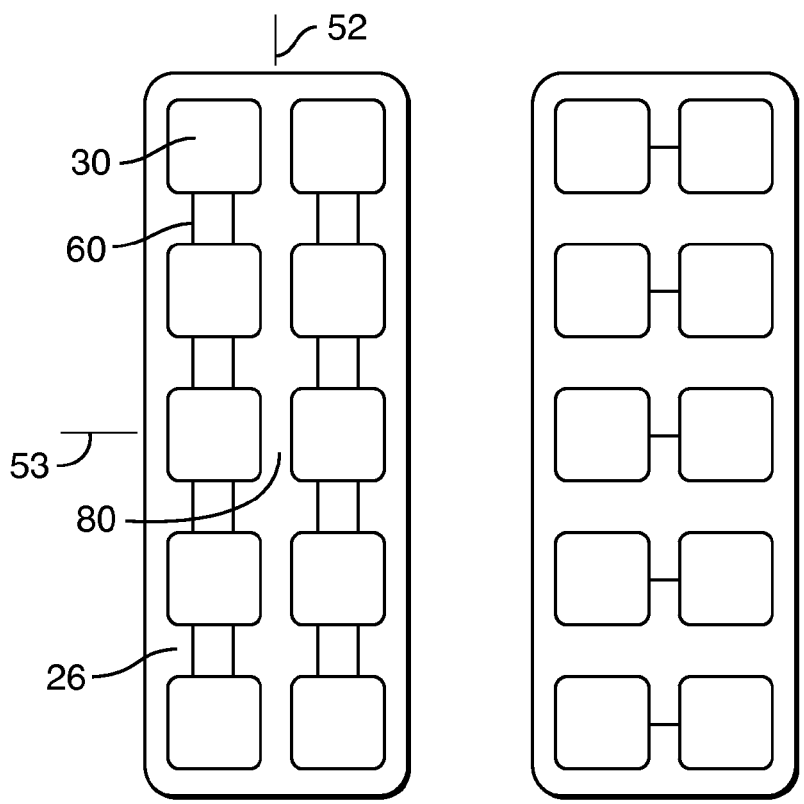
Figures 16C, 16D:
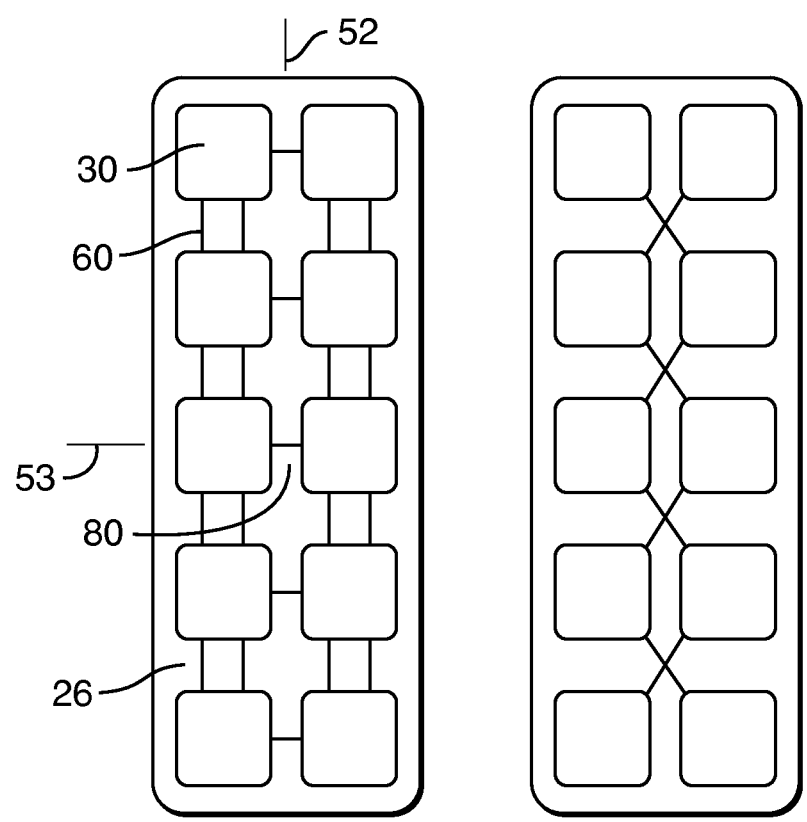

FIGS. 5a-d are top views of a barrier structure illustrating various stitching patterns having varying frequencies according to various embodiments of the present invention;

FIGS. 6a-c are top views of a barrier structure illustrating various stitching patterns having varying amplitudes according to various embodiments of the present invention;

FIGS. 7a-b are top views of a barrier structure illustrating various stitching patterns according to various embodiments of the present invention;

FIG. 8 is a top view of a barrier structure illustrating shrinkable strings disposed in two different stitching patterns;

FIGS. 9a-b are top views of a barrier structure illustrating concave and convex stitching patterns;

FIGS. 10a-c are top views of a barrier structure illustrating various combinations of fluid shrinkable string and embossing patterns disposed on the barrier structure;

FIGS. 11a-c are top views of a barrier structure illustrating various combinations of fluid shrinkable string and embossing patterns disposed on the barrier structure;

FIGS. 12a-c are top views of a barrier structure illustrating various combinations of fluid shrinkable string and embossing patterns disposed on the barrier structure;

FIG. 13 is a top view of a barrier structure illustrating a fluid shrinkable string that has been nicked;

FIGS. 14a-d are top views of a barrier structure illustrating various fluid shrinkable string stitching patterns;

FIGS. 15a-c are top views of various embodiments of an absorbent article having two absorbent layers connected by a fluid shrinkable string; and FIGS. 16a-d are top views of various embodiments of an absorbent article having a plurality of absorbent layers connected by a fluid shrinkable string.

Repeated use of reference characters in the present specification and drawings is intended to represent the same or analogous features or elements of the present invention.

DEFINITIONS

It should be noted that, when employed in the present disclosure, the terms "comprises," "comprising" and other derivatives from the root term "comprise" are intended to be open-ended terms that specify the presence of any stated features, elements, integers, steps, or components, and are not intended to preclude the presence or addition of one or more other features, elements, integers, steps, components, or groups thereof.

The term "absorbent article" generally refers to devices which can absorb and contain fluids. For example, personal care absorbent articles refer to devices which are placed against or near the skin to absorb and contain the various fluids discharged from the body. The term includes, but is not limited to, absorbent articles such as diapers, diaper pants, baby wipes, training pants, absorbent underpants, child care pants, swimwear, and other disposable garments; feminine care products including sanitary napkins, wipes, menstrual pads, menstrual pants, panty liners, panty shields, interlabials, tampons, and tampon applicators; adult-care products including wipes, pads such as breast pads, containers, incontinence products, and urinary shields; clothing components; bibs; athletic and recreation products; and the like.

The term "bond" and its derivatives refer to the joining, adhering, connecting, attaching, sewing together, or the like, of two elements. Two elements will be considered to be bonded together when they are bonded directly to one another or indirectly to one another, such as when each is directly bonded to intermediate elements. "Bond" and its derivatives include permanent, releasable, or refastenable bonding.

The term "complex liquid" describes a liquid generally characterized as being a viscoelastic liquid comprising multiple components having inhomogeneous physical and/or chemical properties. It is the inhomogeneous properties of the multiple components that challenge the efficacy of an absorbent or adsorbent material in the handling of complex liquids. In contrast with complex liquids, simple liquids, such as, for example, urine, physiological saline, water and the like are generally characterized as being relatively low-viscosity and comprising one or more components having homogeneous physical and/or chemical properties. As a result of having homogeneous properties, the one or more components of simple liquids behave substantially similarly during absorption or adsorption, although some components of the simple liquids may be absorbed or adsorbed more readily than others. Although a complex liquid is generally characterized herein as including specific components having inhomogeneous properties, each specific component of a complex liquid generally has homogeneous properties. Consider, for example, a representative complex body-liquid having three specific components: red blood cells, blood protein molecules and water molecules. Upon examination, one skilled in the art could easily distinguish between each of the three specific components according to their generally heterogeneous properties. Moreover, when examining a particular specific component such as the red blood cell component, one skilled in the art could easily recognize the generally homogeneous properties of the red blood cells.

The term "connect" and its derivatives refer to the joining, adhering, bonding, attaching, sewing together, or the like, of two elements. Two elements will be considered to be connected together when they are connected directly to one another or indirectly to one another, such as when each is directly connected to intermediate elements. "Connect" and its derivatives include permanent, releasable, or refastenable connection. In addition, the connecting can be completed either during the manufacturing process or by the end wearer.

The terms "disposed on," "disposed along," "disposed with," or "disposed toward" and variations thereof are intended to mean that one element can be integral with another element, or that one element can be a separate structure bonded to or placed with or placed near another element.

The term "fluid shrinkable string" refers to any material, such as a yarn, fiber, filament, tape, film, nonwoven, laminate, and the like, that is dimensionally stable at normal body temperatures of approximately 37° C. in the dry state, but is dimensionally unstable (i.e. shrinks or distorts) when contacted by a fluid (i.e., any material whether in gaseous or liquid form that is flowable) at the same temperature.

These terms may be defined with additional language in the remaining portions of the specification.

DETAILED DESCRIPTION

Absorbent composites of this invention are useful in absorbent articles, such as disposable absorbent articles. An absorbent article of the present invention can have an absorbent core, and can additionally include a topsheet and/or a backsheet, where the absorbent core can be disposed between the topsheet and the backsheet. The articles can further include leakage barrier structures. In addition, the articles further comprise fluid shrinkable string. The barrier structures present in the article have the ability to stay flat before usage, thus increasing the level of comfort to the user. Upon fluid insult, the fluid shrinkable string, a portion of which is positioned within the barrier structure(s), shrinks and pulls the structures inward (i.e., toward the longitudinal and/or transverse centerline of the article), causing it to lift and activate to a desired shape, forming a closer body fit. With the closer body fit, fluid has a greater tendency to be maintained within the pad, reducing the possibility of leakage.

To gain a better understanding of the present invention, attention is directed to the figures for exemplary purposes showing a feminine care article of the present invention. It is understood that the present invention is suitable for use with various other personal care absorbent articles without departing from the scope of the present invention.

In one embodiment the absorbent article may be a feminine care article such as a feminine care pad or napkin. The article can have a lengthwise, longitudinal direction which can extend along an appointed y-axis of the article, and a transverse, laterally extending, cross direction which can extend along an appointed x-axis of the article. Additionally, the article can include first and second longitudinally opposed end portions, and an intermediate portion located between the end portions. Generally stated, the intermediate portion can be located approximately about the midpoint of an overall, longitudinal length of the article. The feminine care pad also has first and second side edges that are the longitudinal sides of the elongated feminine care pad 20.

The side edges can be contoured to match the shape of the article 20. The article 20 can have any desired shape. The feminine care article can, for example, have a dog bone shape, a race track shape, an hourglass shape, a multi-lobal shape or the like. Additionally, the article can be substantially, longitudinally symmetric, or may be longitudinally asymmetric, as desired.

Figure 1:
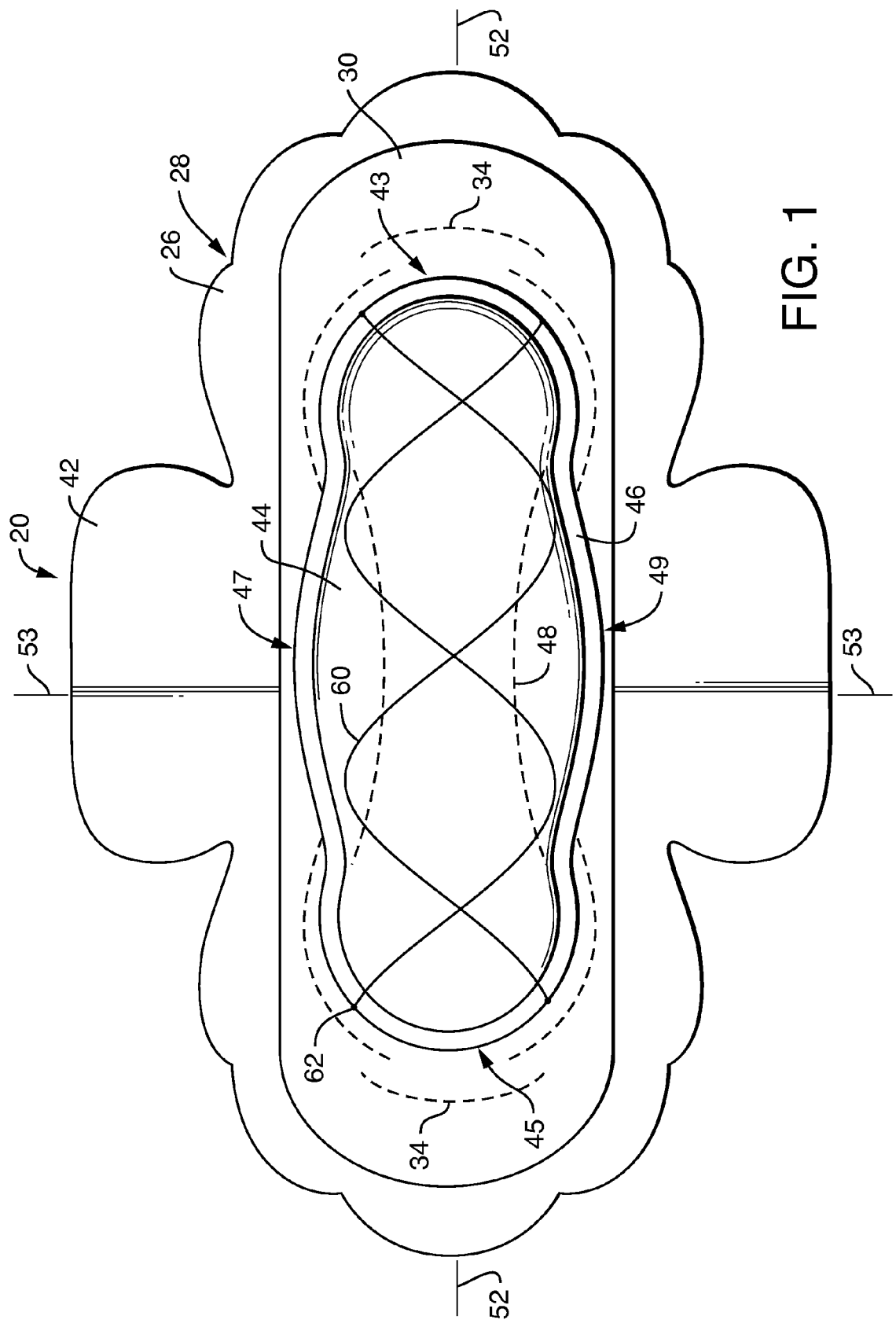
FIG. 1 is a top view of one embodiment of an absorbent article according to the present invention.

As representatively shown in FIG. 1, the absorbent article may be a feminine care pad having a longitudinal dimension that is relatively larger than the transverse (lateral) dimension of the article. Particular configurations of the absorbent article can include one or more optional body facing sheet(s) or cover(s) 26 (also referred to as a topsheet), and/or an optional baffle or backsheet 28. The article has a first major surface which forms a body-facing (bodyside) surface and a second major surface disposed distally from the first major surface 21 which forms a garment-facing surface of the absorbent article. In some aspects, a cover is present which can comprise the first major surface 21 of the absorbent article. In some aspects, a backsheet is present which can comprise the second major surface 23 of the article.

Additionally, an absorbent core 30 can be present in the absorbent article. In aspects where a cover and backsheet are present, the absorbent core 30 can be positioned between the cover and backsheet. In desired arrangements, the cover can be liquid-permeable, and the backsheet can be operatively liquid-impermeable. In other arrangements, the backsheet can provide an additional permeable outercover of the article positioned over a liquid impermeable layer. As representatively shown, for example, peripheries of the cover and backsheet may be substantially entirely coterminous. Alternatively, the peripheries of the cover 26 and the backsheet 28 may be partially or entirely non-coterminous.

The cover 26 may include a layer constructed of any operative material, and may be a composite material. For example, the cover layer can include a woven fabric, a nonwoven fabric, a polymer film, a film-fabric laminate, or the like, as well as combinations thereof. Examples of a suitable nonwoven fabric include spunbond fabric, meltblown fabric, coform fabric, carded web, bonded-carded-web, bicomponent spunbond fabric, or the like, as well as combinations thereof. Other examples of suitable materials for constructing the cover layer can include rayon, bonded-carded webs of polyester, polypropylene, polyethylene, nylon, or other heat-bondable fibers, polyolefins, such as copolymers of polypropylene and polyethylene, linear low-density polyethylene, aliphatic esters such as polylactic acid, finely perforated film webs, net materials, and the like, as well as combinations thereof. In desired arrangements, the cover layer can be configured to be operatively liquid-permeable.

A more particular example of a suitable cover layer material can include a bonded-carded-web composed of polypropylene and polyethylene, such as has been used as a cover stock for KOTEX brand pantiliners. Other examples of suitable materials are composite materials of a polymer and a nonwoven fabric material. The composite materials are typically in the form of integral sheets generally formed by the extrusion of a polymer onto a web of spunbond material. In a desired arrangement, the cover 26 can be configured to be operatively liquid-permeable with regard to the liquids that the article is intended to absorb or otherwise handle. The operative liquid-permeability may, for example, be provided by a plurality of pores, perforations, apertures or other openings, as well as combinations thereof, which are present or formed in the cover layer. The apertures or other openings can help increase the rate at which bodily liquids can move through the thickness of the cover layer and penetrate into the other components of the article (e.g. into the absorbent core 30).

The selected arrangement of liquid-permeability is desirably present at least on an operative portion of the cover that is appointed for placement on the body side of the article. The cover 26 can provide comfort and conformability, and can function to direct bodily exudates away from the body and toward the absorbent core 30. In a desired feature, the cover 26 can be configured to retain little or no liquid in its structure, and can be configured to provide a relatively comfortable and non-irritating surface next to the body tissues of a female wearer. The cover 26 can be constructed of any material which is also easily penetrated by bodily fluids that contact the surface of the cover layer.

The cover 26 can also have at least a portion of its bodyside surface treated with a surfactant and/or a menses modifier to increase the surface energy of the material surface or reduce the viscoelastic properties of the menses, and to render the cover more hydrophilic and more wettable to body fluids. The surfactant can permit arriving bodily liquids to more readily penetrate the cover layer. The surfactant may also diminish the likelihood that the arriving bodily fluids, such as menstrual fluid, will flow off the cover layer rather than penetrate through the cover layer into other components of the article (e.g., into the absorbent core structure). In a particular configuration, the surfactant can be substantially evenly distributed across at least a portion of the upper, bodyside surface of the cover 26 that overlays the upper, bodyside surface of the absorbent.

The cover 26, if present, may be maintained in secured relation with the absorbent core 30 by bonding all or a portion of the adjacent surfaces to one another. A variety of bonding articles known to one of skill in the art may be utilized to achieve any such secured relation. Examples of such articles include, but are not limited to, the application of adhesives in a variety of patterns between the two adjoining surfaces, entangling at least portions of the adjacent surface of the absorbent with portions of the adjacent surface of the cover, or fusing at least portions of the adjacent surface of the cover to portions of the adjacent surface of the absorbent.

The cover 26 typically extends over the upper, bodyside surface of the absorbent core, but can alternatively extend around the article to partially or entirely surround or enclose the absorbent core. Alternatively, the cover 26 and the backsheet 28 can have peripheral margins which extend outwardly beyond the terminal, peripheral edges of the absorbent core 30 and the extending margins can be joined together to partially, or entirely, surround or enclose the absorbent core.

The backsheet 28 may include a layer constructed of any operative material, and may or may not have a selected level of liquid-permeability or liquid-impermeability, as desired. In a particular configuration, the backsheet 28 may be configured to provide an operatively liquid-impermeable backsheet structure. The backsheet may, for example, include a polymeric film, a woven fabric, a nonwoven fabric, or the like, as well as combinations or composites thereof. For example, the backsheet may include a polymer film laminated to a woven or nonwoven fabric. In a particular feature, the polymer film can be composed of polyethylene, polypropylene, polyester, or the like, as well as combinations thereof. Additionally, the polymer film may be micro-embossed. Desirably, the backsheet 28 can operatively permit a sufficient passage of air and moisture vapor out of the article, particularly out of an absorbent (e.g. storage or absorbent core 30) while blocking the passage of bodily liquids. An example of a suitable backsheet material can include a breathable, microporous film, such as a HANJIN Breathable Backsheet available from Hanjin Printing, Hanjin P&C Company Limited, Republic of South Korea.

In a particular feature, the polymer film can have a minimum thickness of no less than about 0.025 mm, and in another feature, the polymer film can have a maximum thickness of no greater than about 0.13 mm Bicomponent films or other multi-component films can also be used, as well as woven and/or nonwoven fabrics which have been treated to render them operatively liquid-impermeable. Another suitable backsheet material can include a closed cell polyolefin foam. For example, closed cell polyethylene foam may be employed. Still another example of a backsheet material would be a material that is similar to a polyethylene film which is used on commercially sold KOTEX brand pantiliners.

The structure of the absorbent core 30 can be operatively configured to provide desired levels of liquid retention and storage capacity, and desired levels of liquid acquisition and distribution. More particularly, the absorbent core can be configured to hold a liquid, such as urine, bowel movement, menses, other complex liquid, or the like, as well as combinations thereof. The absorbent core can include a matrix of absorbent fibers and/or absorbent particulate material to form a stabilized structure and the absorbent fiber can include natural and/or synthetic fiber. The absorbent core may also include one or more components that can modify menses or inter-menstrual liquids.

The absorbent core 30 may also include superabsorbent material. Superabsorbent materials suitable for use in the present invention are known to those skilled in the art, and may be in any operative form, such as particulate form. Generally stated, the superabsorbent material can be a water-swellable, generally water-insoluble, hydrogel-forming polymeric absorbent material, which is capable of absorbing at least about 10, desirably about 30, and possibly about 60 times or more its weight in physiological saline (e.g., 0.9 wt % NaCl). The hydrogel-forming polymeric absorbent material may be formed from organic hydrogel-forming polymeric material, which may include natural material such as agar, pectin, and guar gum; modified natural materials such as carboxymethyl cellulose, carboxyethyl cellulose, and hydroxypropyl cellulose; and synthetic hydrogel-forming polymers. Synthetic hydrogel-forming polymers include, for example, alkali metal salts of polyacrylic acid, polyacrylamides, polyvinyl alcohol, ethylene maleic anhydride copolymers, polyvinyl ethers, polyvinyl morpholinone, polymers and copolymers of vinyl sulfonic acid, polyacrylates, polyacrylamides, polyvinyl pyridine, and the like. Other suitable hydrogel-forming polymers include hydrolyzed acrylonitrile grafted starch, acrylic acid grafted starch, and isobutylene maleic anhydride copolymers and mixtures thereof. The hydrogel-forming polymers are preferably lightly crosslinked to render the material substantially water insoluble. Crosslinking may, for example, be by irradiation or covalent, ionic, Van der Waals, or hydrogen bonding. Suitable materials are available from various commercial vendors, such as Evonik Stockhausen, Inc., a business having offices located in Greensboro, N.C., USA. The superabsorbent material may desirably be included in an appointed storage or retention portion of the absorbent core, and may optionally be employed in other components or portions of the absorbent article.

The amount of superabsorbent material in a selected layer or other component (e.g., the absorbent core 30) can be at least a minimum of about 1 wt %. The amount of superabsorbent material can alternatively be at least about 5 wt %, and can optionally be at least about 8 wt % to provide improved performance. In other aspects, the amount of superabsorbent material can be up to a maximum of about 75 wt %, or more. The amount of superabsorbent material can alternatively be up to about 35 wt %, and can optionally be up to about 20 wt % to provide improved effectiveness.

If the amount of superabsorbent is outside the desired values, there can be excessive leakage. If the amount of superabsorbent is too high, there can be a poor containment of the superabsorbent gel and an excessive amount of gel on the wearer's skin. Additionally, the transfer of liquid to the shaping layer may be inhibited or the product may have an inadequate rate of liquid intake, causing leakage and excessive wetness against the wearer's skin. The manufacturing costs can also become excessive.

In desired configurations, the absorbent core 30 can be included in a feminine care article and can be configured to provide any operative absorbent capacity. In particular arrangements, for example, the absorbent core can provide a total, overall absorbent saturation capacity of up to about 5 grams of menses stimulant. In other arrangements, the absorbent core can provide a total, overall absorbent saturation capacity which is at least a minimum of about 5.5 grams of menses simulant. The overall saturation capacity can alternatively be at least about 25 grams, and can optionally be at least about 40 grams of menses simulant to provide improved performance. In a desired arrangement, the total saturation capacity of the absorbent core 30 can be up to about 107 grams of menses simulant, or more.

A suitable menses simulant is composed of swine blood diluted with swine plasma to provide a hematocrit level of 35% (by volume). A suitable device for determining the hematocrit level is a HEMATOSTAT-2 system, available from Separation Technology, Inc., Altamonte Springs, Fla., USA. Alternatively, a substantially equivalent device or system may be employed.

The specific saturation capacity and the specific retention capacity can be determined by soaking a 1 inch by 1 inch (2.54 cm×2.54 cm) sample of absorbent material in an amount of menses simulant that is sufficient to fully saturate the sample (e.g., 30 mL) for 30 minutes. The wet absorbent is then placed between a layer of through-air-bonded-carded web material and a layer of blotter paper, and a pressure of 0.05 psi (0.345 KPa) is applied for one minute to remove any pools of liquid. The saturated sample is then weighed. The weight of liquid held in the sample divided by the dry weight of the sample is the specific saturation capacity of the sample.

After the saturated sample is weighed, the absorbent sample is placed in a centrifuge and spun at 300 G for three minutes. The spun sample is then weighed. The weight of the liquid remaining in the spun sample divided by the dry weight of the sample is the specific retention capacity of the sample.

Accordingly:

Saturation Capacity=(Wet Wt. Before Centrifuge−Dry Wt.)/(Dry Wt.)

Retention Capacity=(Wet Wt. After Centrifuge-Dry Wt.)/(Dry Wt.)

The total absorbent saturation capacity of an overall layer or other component can be determined by multiplying its specific saturation capacity times the total weight of such component. Similarly, total absorbent retention capacity of an overall layer or other component can be determined by multiplying its specific retention capacity times the total weight of such component.

A suitable through-air-bonded-carded web material has a 2.5 osy (84.8 g/m$^2$) basis weight, a 0.024 g/cm$^3$ density, and is composed of 60 wt % of 6 denier, KoSa type 295 polyester fiber; and 40 wt % of 3 denier, Chisso ESC-HR6 bicomponent fiber. The polyester fiber is available from KoSa, Charlotte, N.C., USA, and the bicomponent fiber is available from Chisso Corporation, Osaka, Japan. A suitable blotter paper is 100-lb white blotter paper. Equivalent materials may optionally be employed.

The absorbent core 30 can be provided by a single unitary layer, or can comprise a composite structure having a selected plurality of component strata or layers. In some aspects, the absorbent core 30 is desirably a stabilized structure.

In some aspects, the article can include at least one side cover. Side covers are an additional strip of cover material that is positioned longitudinally along a longitudinal side edge of the article so as to create a dual cover topsheet layer. Side covers are often hydrophobic, but they need not be. Suitable materials for side covers include a fibrous material formed from fusible polymeric fibers or filaments and non-wovens laminated on a film layer. The side cover can be nonperforated, although a perforated web can be used if desired. The side cover can be formed from various polymers, including polyamides, polyesters, polyolefins, polyvinyl acetate, polyvinyl chloride, polyvinyl alcohol, cellulose acetate, viscose, and the like. Suitable materials include polypropylene spunbond and bonded carded webs. In some aspects, the side cover has a uniform web with a denier of about 1.5 or greater. Side covers are also discussed in U.S. Pat. No. 5,415,640, which is incorporated herein by reference in a manner that is consistent herewith.

In some aspects of the invention, the article 20 can include a system of side panel or wing portions 42. The side panels can be unitarily formed from a selected component of the article, such as the cover and/or the backsheet, and are integrally connected to appointed sections of the side regions along the intermediate portion 76 of the article. Alternatively, the side panels or wings can be separately provided members that are subsequently attached or otherwise operatively joined to the intermediate portion of the article 20.

The side panels can have an appointed storage position (not shown) in which the side panels 42 are directed generally inwardly toward the longitudinally-extending centerline 52. In some aspects, the side panel that is connected to one side margin may have sufficient cross-directional length to extend and continue past the centerline 52 to approach the laterally opposite side margin of the article. The storage position of the side panels can ordinarily represent an arrangement observed when the article is first removed from its wrapper or other packaging. Prior to placing the article into a bodyside of an undergarment prior to use, the side panels 42 can be selectively arranged to extend laterally from the side regions of the article's intermediate portion. After placing the article in the undergarment, the side panels 42 can be operatively wrapped and secured around the side edges of the undergarment to help hold the article in place, in a manner well known in the art.

The side panel portions 42 can have any operative construction and can include a layer of any operative material. Additionally, each side panel can comprise a composite material. For example, the side panels may include a spunbond fabric material, a bi-component spunbond material, a necked spunbond material, a neck-stretched-bonded-laminate (NBL) material, a meltblown fabric material, a bonded carded web, a thermal bonded carded web, a through-air bonded carded web, or the like, as well as combinations thereof.

Each side panel 42 can be joined to its corresponding side region of the article in any operative manner. For example, the side panel can be joined to the cover 26, the backsheet 28 or another article component, as well as any combination thereof. As seen in FIG. 1, for example, each side panel 42 is joined to the outward, garment-side surface of the backsheet 28, but may optionally be joined to the bodyside surface of the backsheet. The side panel can be attached with hot melt adhesive, but any other operative adhesive or attachment mechanism may alternatively be employed.

In another feature, each side panel portion 42, or any desired combination of the employed side panel portions, can include a panel-fastener component which is operatively joined to an appointed engagement surface of its associated side panel. The panel-fastener component can include a system of interengaging mechanical fasteners, a system of adhesive fasteners, or the like, as well as combinations thereof.

In certain embodiments each side panel 42 can include a cooperating component of an interengaging mechanical fastener system. The component can be a "male" component (e.g., a hook component) of the fastener system. Any operative hook component may be employed. For example, a suitable hook component material can include a J-hook, mushroom-head hook, flat-top nail-head hook, a palm-tree hook, a multiple-J hook, or the like, as well as combinations thereof. Alternatively, either or both side panels 42 can include a panel-fastener system which incorporates an operative adhesive. The adhesive may be a solvent-base adhesive, a hot melt adhesive, a pressure-sensitive adhesive, or the like, as well as combinations thereof.

An operative first section of the selected hook component can be joined to a major facing surface of at least a first side panel portion 42 and can be configured to contact or otherwise engage a second side panel portion during ordinary use. Additionally, an operative second section of a hook component, composed of the same or different type of hook material, can be joined to a major facing surface of the second side panel portion and can be configured to contact or otherwise engage an outward surface of the wearer's undergarment during ordinary use. For example, the hook component can be arranged to operatively engage and removably attach to the outward surface of a crotch region of the undergarment.

Each side panel portion 42, or any desired combination of the employed side panel portions, can include a loop or other "female" component of an interengaging mechanical fastener system. Any operative loop component may be employed. For example, a suitable loop component material can include a woven fabric, a knit fabric, a nonwoven fabric, a fabric laminated to a substrate, or the like, as well as combinations thereof.

An operative first section of a selected loop component can be joined to a major facing surface of at least the second side panel portion and can be configured to contact or otherwise engage the hook component on the first side panel portion 42 during ordinary use. Additionally, an operative second section of a loop component, composed of the same or different type of loop material, can be joined to a major facing surface of the first side panel portion 42. As a result, the user can have the option of alternatively attaching the second hook component of the second side panel onto the second loop component of the first side panel. Accordingly, the hook component may alternatively be engaged with the outward surface of the wearer's undergarment.

Each or any desired combination of the provided loop components may be a separately provided member that is subsequently joined and assembled to its corresponding side panel portion. In a desired feature, each or any desired combination of the provided loop components can be integrally provided by the material employed to construct its corresponding side panel portion.

In the various arrangements of the present invention, the hook component can be configured to have a particularly selected hook concentration or density (hooks per unit area). In a particular aspect, the hook density can be at least a minimum of about 1500 hooks/in$^2$ (about 232 hooks/cm$^2$). The hook density can alternatively be at least about 2000 hooks/in$^2$ (about 310 hooks/cm$^2$) and can optionally be at least about 3000 hooks/in$^2$ (about 465 hooks/cm$^2$) to provide improved performance. In another aspect, the hook density may not exceed about 7000 hooks/in$^2$ (about 1085 hooks/cm$^2$). The hook density can alternatively not exceed about 6000 hooks/in$^2$ (about 930 hooks/cm$^2$) and can optionally not exceed about 5000 hooks/in$^2$ (about 775 hooks/cm$^2$) to provide improved performance.

Examples of suitable hook materials can include 85-Series and 61-Series hook materials available from Velcro, USA, Manchester, N.H. The hook materials can have a hook density of about 775 hooks/cm$^2$.

In a particular aspect, the material of the loop component may include a nonwoven fabric having continuous bonded areas defining a plurality of discrete unbonded areas. The fibers or filaments within the discrete unbonded areas of the fabric are dimensionally stabilized by the continuous bonded areas that encircle or surround each unbonded area, such that no support or backing layer of film or adhesive is required. The unbonded areas are specifically designed to afford spaces between fibers or filaments within the unbonded area that remain sufficiently open or large to receive and engage hook elements of the complementary hook material. In particular, a pattern-unbonded nonwoven fabric or web may include a spunbond nonwoven web formed of single component or multi-component melt-spun filaments. At least one surface of the nonwoven fabric can include a plurality of discrete, unbonded areas surrounded or encircled by continuous bonded areas. The continuous bonded areas dimensionally stabilize the fibers or filaments forming the nonwoven web by bonding or fusing together the portions of the fibers or filaments that extend outside of the unbonded areas into the bonded areas, while leaving the fibers or filaments within the unbonded areas substantially free of bonding or fusing. The degree of bonding or fusing within the bonding areas desirably is sufficient to render the nonwoven web non-fibrous within the bonded areas, leaving the fibers or filaments within the unbonded areas to act as "loops" for receiving and engaging hook elements. Examples of suitable point-unbonded fabrics are described in U.S. Pat. No. 5,858,515, the entire disclosure of which is hereby incorporated by reference in a manner that is consistent herewith.

The complementary components of the mechanical fastener are configured to provide a selected attachment peel-force value. In a particular aspect, the peel-force value can be at least a minimum of about 75 grams (g). The peel-force value can alternatively be at least about 100 g and can optionally be at least about 150 g to provide improved performance. In other aspects, the peel-force value can be up to a maximum of about 300 g, or more. The peel-force value can alternatively be up to about 250 g and can optionally be up to about 225 g to provide improved effectiveness.

The complementary components of the mechanical fastener are also configured to provide a selected attachment shear-force value. In a particular aspect, the shear-force value can be at least a minimum of about 1000 g. The shear-force value can alternatively be at least about 1250 g and can optionally be at least about 1500 g to provide improved performance. In other aspects, the shear-force value can be up to a maximum of about 3500 g, or more. The shear-force value can alternatively be up to about 3000 g and can optionally be up to about 2000 g to provide improved effectiveness.

If the peel-force and/or the shear-force are outside the desired values, the fasteners may experience premature unfastening, or may be too difficult to unfasten to remove the article 20 from an associated undergarment.

In the construction of the article 20, the various components may be assembled and held together with any operative securement mechanism or system. For example, the desired attachments or securements can include adhesive bonds, cohesive bonds, thermal bonds, ultrasonic bonds, pins, snaps, staples, rivets, stitches, welds, zippers, or the like, as well as combinations thereof.

The article of the present invention includes at least one barrier structure. The barrier structure serves to establish a barrier to leakage from the article, such as side leakage for example, and can help keep the body-facing surface of the feminine care pad and the underlying absorbent material in close proximity to the wearer's body. The barrier structure can be provided in a number of forms, including as a separate structure or as an integrated structure. By integrated structure, it is meant that the barrier structure is located within the pad, rather than being attached as an isolated component to the body-facing surface of the absorbent article.

In one aspect of the invention, the feminine care pad 20 shown in FIG. 1 is provided with a flat barrier structure 44. If the barrier structure has a radius of curvature, then the radius of curvature toward the wearer's body may be, for example, about 5 mm. However, in some desirable aspects, the barrier structure is relatively flat so as not to draw the attention of the wearer when preparing for use. If the barrier structure 44 is flat, then the radius of curvature is effectively zero.

The barrier structure can have any shape that is desired. For example, in one aspect, the barrier structure 44 has an oval shape, such as illustrated in FIG. 1. The barrier 44 in this aspect is defined by a continuous peripheral edge 46, a longitudinally-extending centerline 52 and transverse-extending centerline 53. In the embodiment illustrated in FIG. 1, the barrier structure 44 is symmetrical about both the transverse 53 and longitudinally 52 extending centerlines, but they need not be.

The barrier structure 44 may be of any caliper. However, in some desirable aspects, the caliper of the barrier structure 44 is less than or equal to about 1.5 mm, more preferably less than about 1 mm or less, so that the total caliper of the feminine care pad 20 is less than about 4 mm, such as less than about 3 mm. It is understood, however, that a thicker barrier structure and thicker feminine care pad can also be provided within the scope of the invention.

The barrier structure can be any length as desired and may be dependent on the size of the article. In a preferred embodiment the barrier structure 44 has a length that is in proportion to the length of the feminine care pad 20. In certain embodiments the length of the barrier structure 44 can range in length from about 25 to about 270 mm, such as from about 50 to about 200 mm to provide improved performance. In one particular aspect, the length of the barrier structure 44 is about 170 mm.

The barrier structure also has a width dimension. The barrier structure can be any width desired, and may be dependent on the size of the article. For example, the barrier structure 44 can range in width from about 5 to about 80 mm, such as from about 30 to about 60 mm to provide improved performance. In one particular aspect, the width of the barrier structure 44 is about 55 mm.

In general, the barrier structure should be flexible enough so that the absorbent article is comfortable to wear. However, the barrier structure should also be stiff enough to maintain leakage barrier properties when activated. For example, in some aspects, the barrier structure should be laterally compressible under relatively low forces so that the absorbent article is comfortable in use. When worn, feminine care pads and other related catamenial products are subjected to lateral compression forces. The barrier structure 44 should be resilient enough so that the feminine care pad should preferably return to its uncompressed state when these compressive forces are released. This ensures that the barrier structure will remain in close body contact once it has been activated.

The barrier structure 44 is preferably liquid pervious and absorbent. Thus, in one aspect of the present invention, when the barrier structure 44 is absorbent, it can provide additional absorbent capacity in the article 20. The barrier structure 44 can be formed from many types of materials. For example, the barrier structure 44 can be formed from soft flexible material such as foam, fluff, paper, nonwoven or the like. For instance, absorbent material such as webs or laminates of absorbent material, with or without superabsorbent materials, can be suitable. Examples of suitable absorbent materials also include webs of cross-linked cellulosic fibers and meltblown webs.

Generally, the barrier structure 44 is attached to the article and preferably to the body-facing side of the cover 26 (if present). In still other aspects, the barrier structure 44 is attached to one of the various other layers or components of the pad 20, such as the absorbent core 30 for example. Attachment of the barrier structure 44 to the article 20 should preferably occur along the longitudinal edge of the barrier structure 44, which is directed generally inwardly toward the longitudinally-extending centerline and/or the transverse-extending centerline of the article 20 (i.e., opposite of the outer edge of the article), depending on the desired configuration of the article, so that the barrier structure 44 can achieve its desired shape when activated.

At least one barrier structure 44 can be located in any desired location on the article 20. Preferably, the barrier structure 44 is located on one side or another of the transverse centerline 53, and/or on at least one side of the longitudinal centerline, such as seen in FIG. 1. In other embodiments, at least one barrier structure 44 can be disposed at various other locations on the article 20, such as oriented in the transverse-extending direction located a distance from one side or another side of the transverse-extending centerline 53 of the article 20, or in a diagonal direction, or any other suitable orientation as desired.

The article of the present invention also includes at least one fluid shrinkable string 60. One skilled in the art will appreciate that while the fluid shrinkable materials of the present invention are generally referred to as strings, they can be in the form of yarn, fiber, filament, tape, film, nonwoven, laminate, and the like. The fluid shrinkable string 60 is capable of activating the barrier structure 44 to its desired shape upon sufficient fluid contact with the fluid shrinkable string 60. In a preferred embodiment, the fluid shrinkable string 60, upon exposure to urine, menstrual fluid or other bodily exudate, will shrink or shorten, thus increasing the tension in the fluid shrinkable string 60. In a particularly preferred embodiment the fluid shrinkable string 60 shrinks or shortens in both water (urine) and menstrual fluid. Preferably upon being contacted by fluid, the length of the string is reduced from about 5% to about 90% and more preferably from about 10% to about 50%. One skilled in the art will appreciate that the degree of shrinkage may vary with the temperature of the fluid. Preferably, it shrinks at the stated level at normal body temperatures of approximately 37° C.

Suitable materials for the fluid shrinkable string 60 include modified polyvinyl alcohol (PVA), modified cellulose fibers (e.g., cotton and rayon), such as carboxymethylated cotton, methylated cotton, ethylated cotton, hydroxyethylated cotton, sulfated cotton, sulfonated cotton, phosphated cotton, cationic cotton, amphoteric cotton, sodium acrylate-, acrylic acid-, acrylonitrile- or acrylamide-grafted cellulose fiber and crosslinked fiber thereof; wool or silk modified in the same manner as described above; modified synthetic fiber, such as a partially saponified acrylonitrile series of fiber and vinilon fiber which is partially esterified by maleic acid, carboxymethylcellulose and hydrolyzed acrylic fiber.

In one particular aspect, a suitable modified PVA fluid shrinkable string can be obtained from Kuraray Group, Japan. Other suitable fluid shrinkable materials include materials capable of rapidly shrinking when coming into contact with water such as those disclosed in U.S. Pat. No. 4,942,089, as well as materials that are dimensionally stable at low to moderate relative humidity, but shrink when exposed at ambient temperatures to relative humidity approaching 100%, such as those disclosed in U.S. Pat. No. 4,839,450. The entire disclosure of U.S. Pat. Nos. 4,942,089 and 4,839,450 are incorporated herein by reference in a manner that is consistent herewith.

In certain aspects, the fluid shrinkable string 60 may include an optional amount of a polyolefin, for example, (PE), polypropylene (PP), polyester (PET) or a combination thereof. Without being bound by any particular theory, it is believed that the inclusion of a polyolefin in the fluid shrinkable string improves attachment of the string to the barrier structure, which may also contain polyolefins. In certain embodiments the fluid shrinkable string can contain up to about 1 wt %, such as up to about 5 wt %, or even up to about 50 wt % or more of a polyolefin. Polyolefins may be incorporated with the modified PVA, for example, by spinning PE, PP, or PET fibers together with the PVA fibers or twisting PE, PP, or PET filaments or yarns together with the PVA filaments or yarns.

In other aspects, the fluid shrinkable string 60 can include an optional amount of moisture absorbing polymer. The polymer can be present in the fluid shrinkable string 60 in an amount as desired, provided that it does not diminish the effectiveness of the shrinkable string. For example, in some aspects, the fluid shrinkable string 60 can contain up to about 1 wt %, such as up to about 5 wt %, or even up to about 10 wt % or more moisture absorbing polymer to provide improved benefits. Examples of suitable moisture absorbing polymers include, but are not limited to, polyethylene oxide, polyethylene glycol, polyvinyl alcohol, polyvinyl pyrolidone, polyvinyl pyridine, or mixtures thereof.

In some aspects, the fluid shrinkable string 60 can include an optional elastomeric polymer. The elastomeric polymer may have permeability for water vapor which can facilitate moisture absorption. The elastomeric polymer component should be present in an amount which is effective to achieve the desired dimensional change properties. The elastomeric polymer can be present in an amount as desired, provided that it does not diminish the effectiveness of the shrinkable string. For example, in some aspects, the fluid shrinkable string 60 can contain up to about 1 wt %, such as up to about 5 wt %, or even up to about 10 wt % or more elastomeric polymer to provide improved benefits. Examples of suitable elastomeric polymers include, but are not limited to, thermoplastic polyurethanes, poly(ether-amide) block copolymers, thermoplastic rubbers such as uncrosslinked polyolefins, styrene-butadiene copolymers, silicon rubbers, synthetic rubbers such as nitrile rubber, styrene isoprene copolymers, styrene ethylene butylenes copolymers, butyl rubber, nylon copolymers, spandex fibers comprising segmented polyurethane, ethylene-vinyl acetate copolymer or mixtures thereof. Preferably, the elastomeric polymer is polyurethane.

A first portion of the fluid shrinkable string 60 is desirably attached to the barrier structure 44 (e.g., attached to the surface of the barrier structure, or attached within the structure). As illustrated in FIG. 1, multiple strings 60 may be attached to the barrier structure 44. The multiple strings can each comprise the same material, or they can comprise different materials. FIG. 1 shows a top view of an article of the present invention, having a structure 44 with three separate fluid shrinkable strings 60 attached thereto, such as with adhesive or embossing, for example. Other means of attachment are contemplated, including, but not limited to, stitching, adhesive bonds, cohesive bonds, thermal bonds, ultrasonic bonds, crimping, entangling, fusing, or the like, and combinations thereof. In some aspects, such bonding can occur over the entire length of the string. However, in other desirable aspects, at least one desirable portion only of the string can be bonded, such as one or more spot welds with adhesives, for example. In some aspects, it is desirable to anchor the ends of the string into the article or barrier structure, while keeping the central length of the string (e.g., the portion between one or more barrier structures) from bonds to provide improved shrinkage performance.

In one exemplary aspect, the fluid shrinkable string 60 is bonded into the barrier structure 44, such as seen in FIG. 1 using a stitching pattern that results in the strings 60 being disposed as intersecting sine wave patterns 60. It is understood that the term "stitching pattern" is not limited to stitching or sewing, but also includes other bonding techniques known in the art. The fluid shrinkable string may also be attached to the barrier structure by anchors 62 disposed at either end of the string to help hold the string pattern in place. In some aspects, the spacing between each string in the longitudinal-extending pattern 60 is approximately equal, though it need not be.

Figure 3:
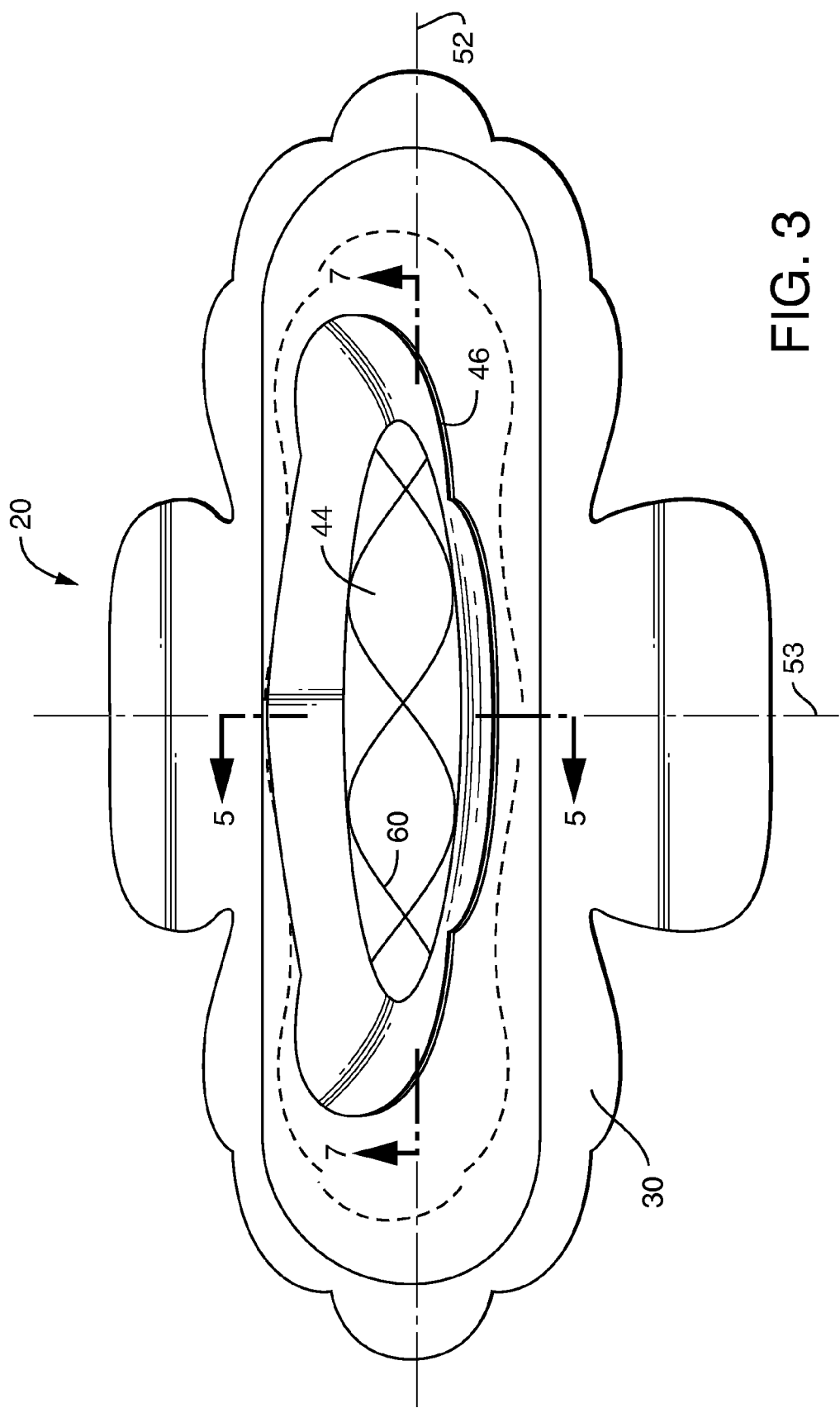
FIG. 3 is a perspective view of an absorbent article according to the present invention after insult by a user.

When menstrual fluid or other bodily exudate contacts one or more points of the fluid shrinkable string 60, the total length of the shrinkable string reduces, which creates a tension. The resulting tension pulls up the periphery of the barrier structure 44 away from the outer edge of the pad 20 inwardly toward the centerline of the pad forming a raised circumferential bank. The raised circumferential bank can take any circumferential shape in its top plan view as long as it forms a closed loop in its top plan view wherein the peripheral edge 46 of the barrier 44 is raised, i.e., higher than its adjacently surrounding element(s) at every portion of the element. Preferred shapes for the raised circumferential bank 50 include an oval (as shown in FIG. 3) and a circle, although any other shapes can be taken, for example, a rectangle including a square, a pentagon, a hexagon, or the like.

Figure 4:
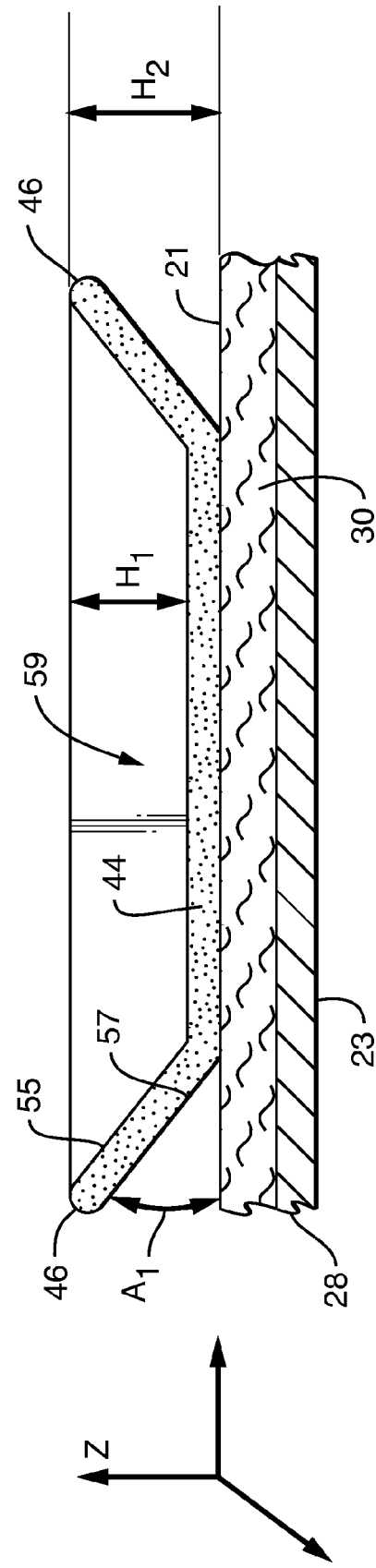
FIG. 4 is a cross sectional view of the absorbent article of FIG. 3 through the line 5-5.

As shown in FIG. 4, the body facing surface 21 of the pad 20 lies adjacent to a barrier structure 44, which forms a raised circumferential bank about the periphery 46 of the barrier 44 and a concave portion 59 surrounded by the raised circumferential bank. The concave portion 59 can take any cross-sectional bottom shape. As illustrated in FIG. 4, in one preferred embodiment the concave portion 59 has a flat cross-sectional bottom shape. In theory the concave portion 59 acts as a reservoir for body fluids and the raised circumferential bank effectively prevents body fluids from flowing over the edge of the bank formed by the peripheral edge 46 of the barrier 44.

The raised circumferential bank has an inside wall 55 and an outside wall 57. As shown in FIG. 4, the outside wall 57 has a slope having an average slope angle A1. The average slope angle A1 is measured from the body facing surface 21 of the outside region of the absorbent core 30 to the outside wall 57, respectively, as shown in FIG. 4. The average slope angle is defined as the average angle value of the respective circumferential slope of the wall. In the pad 20 shown in FIG. 4, the outside wall 57 of the raised circumferential bank has an average slope angle A1 of from about 10 degrees to about 150 degrees and more preferably from about 30 degrees to about 60 degrees.

As further illustrated in FIG. 4, the raised circumferential bank has a height H1 which is measured from the body facing surface 21 to the peripheral edge 46. In a preferred embodiment, the raised circumferential bank has a height H1 of at least about 1 mm, preferably between about 2 and about 40 mm, and more preferably between about 3 and about 20 mm. The concave portion 59 has a depth D1 which is measured from the top of the peripheral edge 46, as shown in FIG. 4. In a preferred embodiment, the raised circumferential bank has a depth D1 of at least about 1 mm, preferably between about 2 and about 40 mm, and more preferably between about 3 and about 20 mm. The distance or angle of lift can be modified as desired according to several factors, including the shrinkage ability of the string material, the string position, the stitching pattern, etc. The result is the deformation of the periphery 46 of the barrier structure 44 resulting in a raised circumferential bank which provides a closer body fit, as well as a barrier to leakage.

With further reference to FIG. 4, when the user insults a fluid shrinkable member, the peripheral regions (front, rear and sides) 46 of the barrier structure 44 are raised from the flat orientation towards the z-direction, forming a circumferential bank. With the body of the user being a natural obstacle to the raising motion, the barrier structure 44 eventually conforms to the user's body. Thus, upon insult the barrier structure 44 is transformed from a substantially flat structure to a structure having some volume. The volume will depend, as described above, upon several factors including the shrinkage ability of the string material, the string position and the stitching pattern. In addition to forming a leakage barrier between the user and the periphery 46 of the barrier structure 44, the circumferential bank facilitates the capture and containment of discharge at the source, preventing leakage all around.

The degree of deformation achieved and the resulting shape of the circumferential bank may be measured using the following test procedure. The product is prepared under TAPPI conditions (50% humidity and 72° F.) for 24 hours. The product is transferred to a flat surface and adhered. Saline, water or swine blood simulant is applied uniformly along the entire longitudinal centerline of the barrier to activate, i.e., deform the barrier. The product is further insulted by the addition of 2 ml of saline to the transverse centerline of the barrier. After five minutes an additional 2 ml of saline is added at a position about 2 cm away from the transverse centerline and towards one end of the barrier layer. After five minutes an additional 2 ml of saline is added at a position about 2 cm away from the transverse centerline and towards the opposite end of the barrier layer. The insulting of the barrier layer is continued, alternating the site of insult and waiting five minutes between insults, until the barrier is completely insulted. The degree of deformation is then measured by measuring the height of the barrier rise at the point of greatest rise and measuring the angle of the barrier rise at the point of greatest rise.

FIG. 1 illustrates one stitching pattern capable of deforming the periphery of the barrier structure; however, other patterns are contemplated. In one embodiment, the stitching pattern comprises pairs of shrinkable members 60 curved in the pattern of a sine wave with varying frequency (FIGS. 5a-d) and amplitude (FIGS. 6a-c), and intersecting along the longitudinal center line 52 of the barrier structure 44. When the shrinkable members 60 are insulted by a user, they shrink and create a mechanical force that pulls on the periphery 46 of the absorbent structure 44 causing it to deform. The mechanical forces experienced by the front 43 and rear 45 edges of the barrier structure are in the longitudinal direction whereas the mechanical forces experienced by the side edges 47, 49 are in the transverse direction. The mechanical forces cause the periphery 46 of the barrier structure 44 to be lifted a distance D in the z-direction, forming a 'cup' shape and allowing it to hug the user's body more closely.

In the embodiment illustrated in FIGS. 5a-d the fluid shrinkable member 60 is stitched in sine wave patterns having varying wavelengths. The wavelength of the sine wave may vary depending on the length of the barrier structure, for example the wavelength may range from about ½ to about 10 and still more preferably from about 2 to about 4. In certain preferred embodiments the fluid shrinkable member is stitched in a sine wave pattern with a frequency of about 4 and still more preferably about 3, such that the amplitude sine wave is about zero near the front 43 and rear 45 of the barrier structure. In still other embodiments, such as those illustrated in FIGS. 6a-c, the amplitude of the stitching pattern 60 may be varied. For example, the amplitude of the sine wave pattern may be varied from about 1 cm to about 10 cm and more preferably from about 2 cm to about 5 cm. The sine wave may be orientated in the longitudinal direction, as illustrated in FIGS. 5a-d, or it may be orientated in the transverse direction.

The sine wave stitching pattern may be formed from a single fluid shrinkable string or one or more strings. For example, as illustrated in FIGS. 7a-b, as the frequency of the wave pattern 60 increases, for example greater than about 3 to 4 wavelengths, a single strand of shrinkable member 60 traversing the absorbent layer 44 from side to side is sufficient to create the cupping effect produced by a pair of intersecting members laid out in the pattern of a low-frequency sine wave. In other embodiments the stitching pattern may be formed from two or more fluid shrinkable strings where the strings have different shrinkage ratios. For example, the periphery of the barrier structure may be deformed by stitching six longitudinal fluid shrinkable strings, whereby strings with higher shrinkage ratio are stitched near the outer edge of the barrier structure and strings with lower shrinkage ratios stitched in the center. Upon fluid contact, the strings near the edge shrink to a greater extent than those in the center, causing the periphery of the barrier structure to rise to a greater extent, thus forming a cup structure.

In another embodiment, the wave pattern can also be laid out in such a manner that the pattern is repeated in the transverse direction, as illustrated in FIGS. 14a-d, as opposed to the longitudinal direction as illustrated in the previous embodiments. As illustrated in FIGS. 14a-d, the fluid shrinkable string 60 may be stitched in wave patterns varying in frequency, amplitude, number of sets of repeating waves along the length of the barrier structure 44, distance between each set of repeating wave, locations of the points of highest and lowest amplitude of the wave on the barrier structure 44 and similar manipulations as described in the previous embodiments.

In still other embodiments, deformation of the periphery 46 of the barrier structure 44 may be accomplished by stitching two or more fluid shrinkable strings 60 in different patterns. For example, as illustrated in FIG. 8, three fluid shrinkable strings 60a, 60b and 60c may be disposed on the barrier structure 44, one string 60c stitched in a low-frequency sine wave pattern and two strings 60a, 60b stitched parallel to one another and to the longitudinal center line 52 of the barrier structure 44.

In another embodiment, it is also possible to vary the curvature of each shrinkable member 60, including varying the curvature of two or more shrinkable members 60 such that they arranged in concave (FIG. 9a) or convex (FIG. 9b) relation to one another.

In still other embodiments the deformation of the periphery of the barrier structure may be facilitated by one or more deformation enhancing elements. Deformation enhancing elements may include, without limitation, embossing and perforations. Deformation enhancing elements may also include adhering the barrier structure and the top sheet with varying patterns and degrees of adhesion. Without being bound by any particular theory, it is believed that embossing the barrier structure controls the level of rise of the peripheral regions of the absorbent later when the regions are engaged by the mechanical forces produced by the shrinking members after contacting fluid. In one embodiment, the embossing pattern can be placed directly over the shrinkable members to impede the shrinking motion when the member is contacted by fluid. In another embodiment, one or more of the shrinkable members can be located on the side of the embossing pattern nearer to the periphery of the barrier structure. The embossing pattern may be of a plain, dotted, hatched or of other designs that will serve to act as a control to the mechanical forces exerted by the shrinkable members. Further, the embossing pattern can be continuous, disjointed, straight or arched and may also vary in the width and depth of embossing, or may be a combination of the above. In addition to performing the control function, the embossing pattern can also serve as a barrier to fluid flow by increasing the difficulty of fluid passage across the pattern. Suitable embossing patterns are illustrated in FIGS. 1 and 10-12.

In certain embodiments the absorbent article may comprise one or more embossing elements. As illustrated in FIG. 1 the embossing elements may be disposed on the absorbent core 30 as absorbent core embossing 34, or alternatively, or in addition to, the barrier structure 44 as barrier structure embossing 48. In those embodiments where embossing is disposed on the barrier structure 44 the embossing 48 may be located entirely within the fluid shrinkable member 60, as illustrated in FIGS. 10a-c, or both within and outside of the fluid shrinkable member 60 as illustrated in FIGS. 11a-c.

In the embodiment illustrated in FIGS. 11a-c, the embossing 48 is used to fix and deactivate the shrinkable members 60 in strategic places on the barrier structure 44 to control the level of rise along the peripheral edge 46. Without being bound by any particular theory, it is believed that embossing, according to the embodiment illustrated in FIGS. 11a-c, allows the fluid-activated barriers to react and rise in a symmetrical fashion even when the various shrinkable members are exposed to different amounts of fluids and shrink to different extents. As an additional benefit, the embossing patterns may also serve to integrate the layers of material that make up the barrier structure so that the barrier structure is thinner and more compact. Embossing in this manner avoids scrunching or creasing of loose material layers along the path of shrinkage of the shrinkable members.

FIGS. 12a-c illustrate still other embodiments in which embossing 48 is used to aid the deformation of the periphery 46 of the barrier structure 44. In the illustrated embodiments, embossing 48 may be disposed in either a curved (FIGS. 12a and 12b) or straight (FIG. 12c) pattern. Embossing may also be disposed in either the transverse (FIG. 12a) or longitudinal direction, or both (FIGS. 10b and 10c) and more preferably disposed about the transverse 52 or longitudinal center lines.

Deformation of the periphery of the barrier structure may also be facilitated by stitching the fluid shrinkable string in a discontinuous pattern. As illustrated in the embodiment shown in FIG. 13, the shrinkable members 60 may be initially deposited in a continuous pattern and then cut to form a discontinuous pattern. Cutting may be achieved by nicking at strategic places with the sharp edge of a blade or via similar methods.

Figure 2:
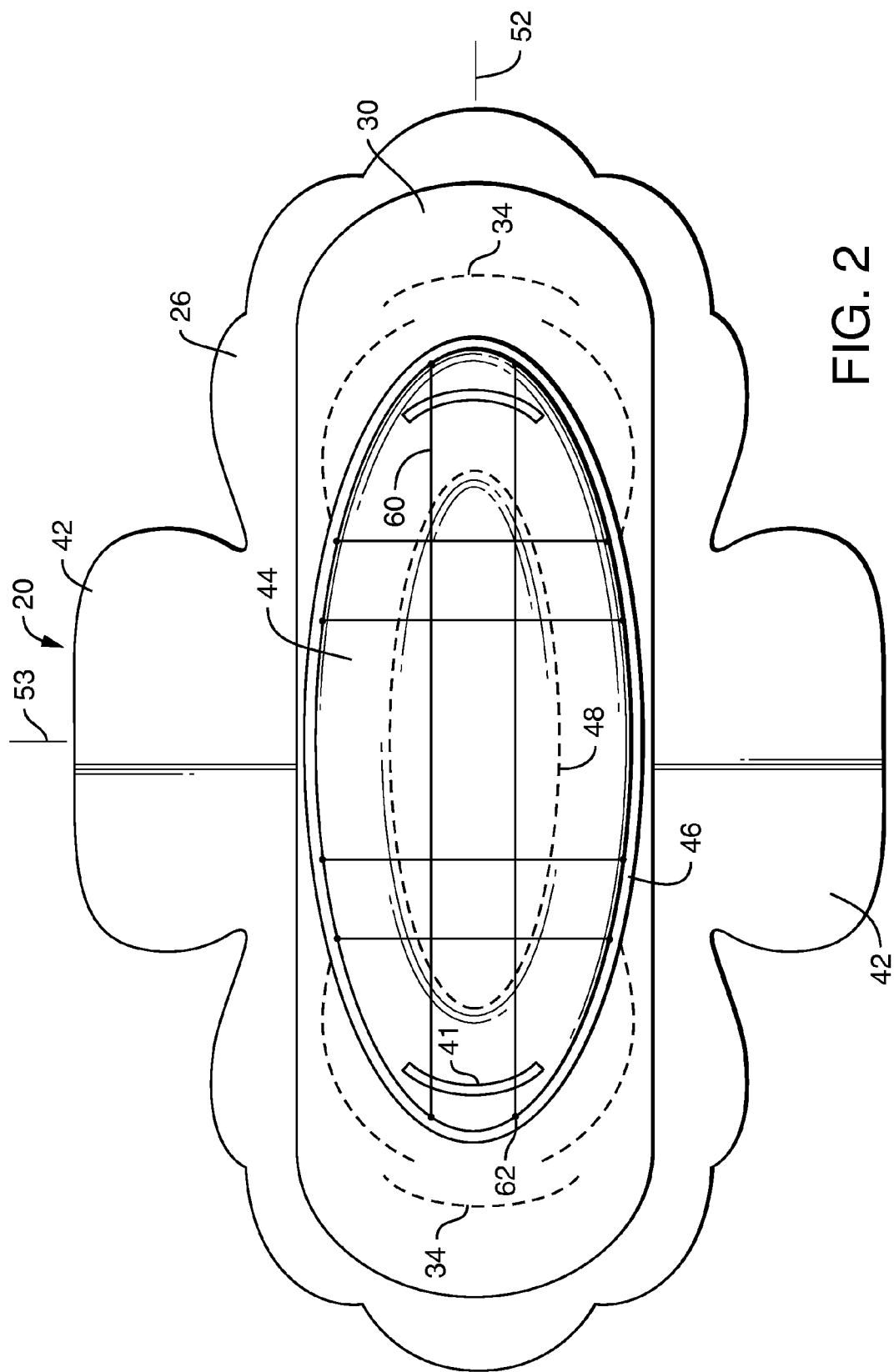
FIG. 2 is a top view of another embodiment of an absorbent article according to the present invention.

In other embodiments the deformation enhancing element may comprise one or more slits or cutouts within the barrier structure. In addition to enhancing deformation, slits may increase absorbency by providing channels for fluid to travel from the barrier structure to an adjacent absorbent layer. The slit may be of any shape, including a rectangle, square, or circle. The longest dimension of the slit may measure from about 1 to about 50 mm in length and more preferably about 1 to about 15 mm in length. The barrier structure may comprise one or more slits, which may be orientated in either the longitudinal or transverse direction. For example, as illustrated in FIG. 2, the barrier structure 44 may comprise a pair of semicircle shaped slits 41 disposed near distal ends 43, 45 of the barrier structure.

In another embodiment, leakage protection is afforded by fluid-activated absorbent structures which change their positions within the absorbent article during use. In one embodiment, illustrated in FIGS. 15a-c, absorbent layers 30a and 30b are sandwiched between a topsheet 26 and a fluid-impermeable backsheet 28. The absorbent layers 30a and 30b can be placed in a transverse orientation on either side of the transverse-extending centerline of the pad 53, as illustrated in FIGS. 15a and 15b, or on either side of the longitudinal-extending centerline of the pad 52, as illustrated in FIG. 15c. The absorbent layers 30a and 30b are connected to one another by fluid shrinkable strings 60, which affixed to the absorbent layers via adhesive, heat bonding or other methods, and can be connected in vertical, horizontal, diagonal, curved or other layouts. Upon fluid insult, the shrinkable members contract and pull the absorbent layers towards each other, creating a fresh absorbent area to capture more insult. The saturated absorbent area is then slowly concealed by the fresh, shifting absorbent layers, thus providing additional dryness for the user.

In another embodiment, the absorbent layers can be further sectioned into two or more discrete absorbent layers and connected to each other by shrinkable members in manners as described in the previous embodiment. Upon fluid insult, the shrinkable members contract in the area of the insult and pull along neighboring absorbent layers. As a result, absorbent capacity is constantly shifting to areas where it is required the most. For example, two or more absorbent layers, more preferably from about 4 to about 10 absorbent layers and still more preferably from about 6 to 8 absorbent layers are disposed about a target zone on the absorbent article. As illustrated in FIGS. 16a-d, for example, ten absorbent layers 30 are positioned about the target zone 80. The individual absorbent layers are preferably connected to one another by fluid shrinkable strings 60. The fluid shrinkable strings 60 can be bonded in both the transverse-extending direction and the longitudinal-extending direction to form a cross-stitching pattern. Upon fluid insult, the shrinkable members 60 contract in the area of the insult and pull along neighboring absorbent layer 30. As a result, absorbent capacity is constantly shifting to areas where it is required the most.

Because the barrier structure of the present invention may be deformed in response to moisture, it is desirable to package the absorbent articles in moisture impervious packaging. Preferably the packaging unit is comprised of film material that has low vapor and gas permeability and tight joints. Suitable packaging is described, for example, in U.S. Pat. No. 6,854,600, the relevant portions of which are incorporated herein by reference. The packaging material used is preferably comprised of several layers, where different layers may consist of different materials. For example, the packaging material may include an inner material that enables a good seal to be obtained, e.g. PE, PP, EVA, EEA or wax, an intermediate material that consists of the moisture-protective barrier material, the impervious layer, e.g. aluminum, aluminum oxide, silicon oxide or polyamide (nylon), and a somewhat stronger outer material that functions as barrier material, e.g. PETP, PE or PP. In order to ensure that the packaging unit is impervious to moisture the package is, preferably, completely closed with tight joints and seams. The packages may optionally include a desiccant, such as silica gel or zeolite.

Although only a few exemplary embodiments of this invention have been described in detail above, those skilled in the art will appreciate that many modifications are possible without materially departing from the novel teachings and advantages of this invention. For example, features described in relation to one embodiment may be incorporated into any other embodiment of the invention. Accordingly, all such modifications are intended to be included within the scope of this invention, which is defined in the following claims and all equivalents thereto. Further, it is recognized that many embodiments may be conceived that do not achieve all of the advantages of some embodiments, particularly of the desirable embodiments, yet the absence of a particular advantage shall not be construed to necessarily mean that such an embodiment is outside the scope of the present invention. As various changes could be made in the above constructions without departing from the scope of the invention, it is intended that all matter contained in the above description shall be interpreted as illustrative and not in a limiting sense.

What is claimed is:

1. An absorbent article configured for controlled deformation when insulted by a user, the absorbent article comprising:
   a. an absorbent core having a garment facing surface and a body facing surface;
   b. a deformable barrier structure positioned adjacent to the body facing surface of the absorbent core, the barrier structure having a longitudinal direction, a transverse direction, a longitudinally-extending centerline, a transverse-extending centerline, and a peripheral edge, the barrier structure further comprising at least one deformation enhancing element selected from the group consisting of embossing and perforation; and
   c. a fluid shrinkable string attached to the deformable barrier structure in a pattern capable of providing forces to the barrier structure in both the longitudinal and transverse direction when insulted by a user.

2. The absorbent article of claim 1 wherein the fluid shrinkable string is attached to the barrier structure at two or more spaced apart points by an attachment means selected from the group consisting of stitching, adhesive bonds, cohesive bonds, thermal bonds, ultrasonic bonds, crimping and embossing.

3. The absorbent article of claim 1 comprising two or more fluid shrinkable strings.

4. The absorbent article of claim 3 wherein at least two fluid shrinkable strings intersect one another.

5. The absorbent article of claim 4 wherein at least one fluid shrinkable string is disposed substantially parallel to the longitudinal direction of the barrier structure and at least one shrinkable string is disposed substantially parallel to the transverse direction of the barrier structure.

6. The absorbent article of claim 4 wherein at least one fluid shrinkable string crosses the longitudinally-extending centerline and at least one fluid shrinkable string crosses the transverse-extending centerline.

7. The absorbent article of claim 1 wherein the fluid shrinkable string is disposed in a sine wave pattern that intersects the longitudinal center line of the barrier structure.

8. The absorbent article of claim 7 wherein the sine wave pattern has a wavelength in the range from about 0 to about 10.

9. The absorbent article of claim 7 wherein the sine wave pattern has an amplitude in the range from about 1 cm to about 3 cm.

10. The absorbent article of claim 3 wherein at least one fluid shrinkable string is present as a sine wave stitching pattern and at least one fluid shrinkable string is present as a longitudinal-extending stitching pattern disposed substantially parallel to the longitudinal center line of the barrier structure.

11. The absorbent article of claim 3 wherein the two or more fluid shrinkable strings are disposed in a longitudinal-extending stitching pattern substantially parallel to the longitudinal center line of the barrier structure.

12. The absorbent article of claim 3 wherein the two or more shrinkable strings have different shrinkage ratios.

13. The absorbent article of claim of 3 wherein the two or more fluid shrinkable strings are present as a concave or convex stitching pattern relative to the longitudinal center line of the barrier structure.

14. The absorbent article of claim 1 wherein the deformation enhancing element is a perforation having a longitudinal axis oriented substantially parallel to the longitudinally-extending centerline of the barrier structure, the perforation having a length from about 1 mm to about 50 mm.

15. The absorbent article of claim 1 wherein the deformation enhancing element is an embossing element that intersects at least one fluid shrinkable string.

16. The absorbent article of claim 1, wherein the barrier structure has an oval, circular, or rectangular shape.

17. An absorbent article configured for controlled deformation when insulted by a user, the absorbent article comprising:
　a. an absorbent core having a garment facing surface and a body facing surface;
　b. a deformable barrier structure adjacent to the body facing surface of the absorbent core, the barrier structure having a peripheral edge and at least one deformation enhancing element selected from the group consisting of embossing and perforation; and
　c. a fluid shrinkable string attached to the deformable barrier structure in a pattern capable of deforming the peripheral edge of the barrier structure in the z-direction to form a raised circumferential bank and a concave portion surrounded by the raised circumferential bank.

18. The absorbent article of claim 17 wherein the raised circumferential bank comprises an inside wall and an outside wall, the outside wall having an average slope angle of from about 10 degrees to about 150 degrees.

19. The absorbent article of claim 17 wherein the raised circumferential bank has a height, measured from the body facing surface of the absorbent core to the peripheral edge of the barrier structure, from about 1 mm to about 40 mm.

20. The absorbent article of claim 17 wherein the barrier structure has a body facing surface and an absorbent core facing surface, and wherein the concave portion has a depth, measured from the peripheral edge of the barrier structure to the body facing surface of the absorbent core, from about 1 mm to about 40 mm.

* * * * *